United States Patent
Lehr

(12) 
(10) Patent No.: US 6,310,217 B1
(45) Date of Patent: Oct. 30, 2001

(54) ACYLPYRROLEDICARBOXYLIC ACIDS AND ACYLINDOLEDICARBOXYLIC ACIDS AND THEIR DERIVATIVES AS INHIBITORS OF CYTOSOLIC PHOSPHOLIPASE $A_2$

(75) Inventor: Matthias Lehr, München (DE)

(73) Assignee: Merckle GmbH, Blaubeuren (DE)

( * ) Notice: Subject to any disclaimer, the term of this patent is extended or adjusted under 35 U.S.C. 154(b) by 0 days.

(21) Appl. No.: 09/240,148

(22) Filed: Jan. 29, 1999

Related U.S. Application Data

(63) Continuation of application No. PCT/EP97/03842, filed on Jul. 17, 1997.

(30) Foreign Application Priority Data

Aug. 1, 1996 (DE) .............................................. 196 31 102

(51) Int. Cl.[7] ...................... C07D 209/10; C07D 209/12; C07D 209/14; C07D 207/32; A61K 31/40; A61K 31/405

(52) U.S. Cl. .......................... 548/492; 548/491; 548/562; 514/419; 514/423

(58) Field of Search .................... 548/491, 492, 548/562

(56) References Cited

U.S. PATENT DOCUMENTS

| | | | |
|---|---|---|---|
| 3,624,103 | 11/1971 | DeMartis et al. | 260/326 |
| 5,081,145 | * 1/1992 | Guindon et al. | 514/419 |
| 5,229,516 | 7/1993 | Musser et al. | 546/172 |
| 5,260,451 | 11/1993 | Dannhardt et al. | 548/453 |
| 5,420,289 | 5/1995 | Musser et al. | 548/159 |
| 5,578,634 | 11/1996 | Bach et al. | 514/419 |
| 5,641,800 | 6/1997 | Bach et al. | 514/415 |

FOREIGN PATENT DOCUMENTS

| | | | |
|---|---|---|---|
| 623469 | 8/1990 | (AU) . | |
| 4325204 A | 2/1995 | (DE) | C07D/207/337 |
| WO95/13266 | 5/1995 | (WO) | C07D/207/32 |

OTHER PUBLICATIONS

Dillard et al., "Indole Inhibitors of Human Nonpancreatic Secretory Phospolipase $A_2$ 1. Indole–3–acetamides", J. Med. Chem., vol.39, No.26, Dec. 20, 1996, pp 5119–5136.

Schevitz et al., "Structure–based design of the first potent and selective inhibitor of human nonpancreatic secretory phospholipase $A_2$", Nat. Struct. Biol., vol. 2, No. 6, 1995, pp 458–465.

Lehr, "3–(Octadecanoylaminomethyl)indole–2–carboxylic Acid Derivatives and 1–Methyl–3–octa–decanoyl–indole–2–carboxylic acid as Inhibitors of Cytosolic Phospholipase $A_2$", Arch Pharm., vol. 329, 8/96, pp 386–392.

Dillard et al., "Indole Inhibitors of Human Nonpancreatic Secretory Phospolipase $A_2$ 1. Indole–3–acetamides with Additional Functionality", J. Med. Chem., vol.39, No.26, Dec. 20, 1996, pp 5137–5158.

Lehr, "Synthesis, Biological Evaluation and Structure–Activity Relationships of 3–Acylindole–2–carboxylic acids as Inhibitors of the Cytosolic Phospholipase $A_2$", J. Med. Chem., vol. 40, No. 17, 8/97, pp 2694–2705.

* cited by examiner

Primary Examiner—Floyd D. Higel
(74) Attorney, Agent, or Firm—Anderson, Kill & Olick, P.C.

(57) ABSTRACT

The invention provides novel antiinflammatory and analgesic agents of the formulae

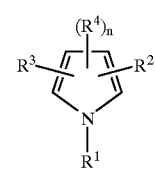

I

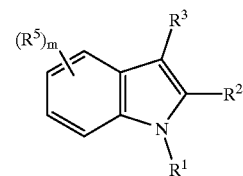

II

The novel compounds have an improved inhibitory effect and/or less cytotoxicity in comparison with compounds known from the prior art. The compounds according to the invention are outstandingly suitable for preventing and/or treating disorders caused or partly caused by an increased activity of the enzyme phospholipase $A_2$, such as, for example, inflammations, allergies, asthma, psoriasis and endotoxic shock.

15 Claims, No Drawings

ACYLPYRROLEDICARBOXYLIC ACIDS AND ACYLINDOLEDICARBOXYLIC ACIDS AND THEIR DERIVATIVES AS INHIBITORS OF CYTOSOLIC PHOSPHOLIPASE $A_2$

This application is a continuation of PCT/EP97/03842 filed Jul. 17, 1997.

The present invention relates to novel acylpyrroledicarboxylic acids and acylindoledicarboxylic acids, and their derivatives, which inhibit the enzyme phospholipase $A_2$. These compounds are suitable as pharmaceuticals for preventing and treating disorders caused or partly caused by an increased activity of this enzyme, such as, for example, inflammations, pain, fever, allergies, asthma, psoriasis and endotoxic shock. The invention further relates to methods for synthesizing these compounds and to pharmaceutical compositions comprising these compounds.

It is known that phospholipase $A_2$ cleaves the ester linkage in position 2 of membrane phospholipids by hydrolysis, producing free fatty acids, mainly arachidonic acid, and lyso-phospholipids.

The liberated arachidonic acid is metabolized by the cyclooxygenase pathway to the prostaglandins and thromboxanes and by the lipoxygenase pathway to the leukotrienes and other hydroxylated fatty acids. The prostaglandins are essentially involved in the production of pain and fever and in inflammatory reactions. Leukotrienes are important mediators in inflammatory processes and in anaphylactic and allergic processes (Forth et al., Allgemeine und Spezielle Pharmakologie and Toxikologie BI Wissenschaftsverlag Mannheim, Vienna, Zurich, 1987).

The lyso-phospholipids formed by phospholipase $A_2$ have cytotoxic properties. Lyso-phosphatidylserine leads to the release of histamine which is involved in allergic processes (Moreno et al., Agents Actions 1992, 36, 258). Lyso-phosphatidylcholine is moreover metabolized to platelet-activating factor (PAF) which is likewise an important mediator, for example in inflammations.

Since phospholipase $A_2$ is the key enzyme for formation of said pathophysiologically significant mediators, these mediator effects can be eliminated by inhibiting the enzyme.

Some pyrrole derivatives have already been disclosed as antiinflammatory and analgesic agents. The effect of the substance tolmetin (5-(4-methylbenzoyl)-pyrrol-2-ylacetic acid) which has already been approved as pharmaceutical (U. Ficke et al. Neue Arzeimittel 1993, Wissenschaftliche Verlagsgesellschaft, Stuttgart 1994, pages 20 et seq.) and the benzoylpyrrolealkanoic acids disclosed in German Published Specification 3,415,321 is based on inhibition of cyclooxygenase. The result of inhibition of cyclooxygenase is that more arachidonic acid, which is synthesized in the preceding step in a reaction catalyzed by phospholipase $A_2$, is available for lipoxygenase metabolism. This further intensifies certain symptoms of inflammation caused by lipoxygenase-dependent arachidonic acid derivatives. German Published Specification 2,302,669 discloses 1-methyl-5-(3-phenylacryloyl)pyrrol-2-ylformic acid as a compound with an analgesic effect in mice.

In addition, some compounds are known as phospholipase $A_2$ inhibitors. WO 88-06,885 discloses aminoalkylamides and EP-A-377 539 discloses 4-aryloyl-pyrrol-2-ylformic acids with an inhibitory effect on phospholipase $A_2$.

Indole-2-alkanoic acids are disclosed as analgesics with an inhibitory effect on prostaglandins and thromboxanes in U.S. Pat. No. 5,081,145. U.S. Pat. No. 5,132,319 describes 1-(hydroxylaminoalkyl)indole derivatives which inhibit leukotriene biosynthesis. This results in these compounds having an analgesic and antiinflammatory effect. The (azaarylmethoxy)indoles disclosed in EP-A-535 923 likewise inhibit leukotriene biosynthesis.

The fact that certain acylpyrrolealkanoic acids and indole-2-alkanoic acids and their derivatives are able to inhibit phospholipase $A_2$ is already known from WO 95/13266. Although the acylpyrrolealkanoic acids and indole-2-alkanoic acids disclosed therein are potent phospholipase $A_2$ inhibitors, there is a need in the specialty for novel compounds having a further improved inhibitory effect and/or less cytotoxicity.

It is therefore the object of the present invention to provide antiinflammatory and analgesic agents which have an improved inhibitory effect and/or less cytotoxicity than compounds known in the prior art. Whereas the antiinflammatory and analgesic effects of nonsteroidal antiinflammatory agents currently available for therapy are based on inhibition of prostaglandin formation resulting from inhibition of the enzyme cyclooxygenase, the claimed substances, like the compounds disclosed in WO 95/13266, are intended to inhibit the enzyme phospholipase $A_2$. This results in suppression not only of the biosynthesis of the prostaglandins involved in inflammatory processes and in the pain process, but also of the formation of leukotrienes, of platelet-activating factor and of lyso-phospholipids.

It has now been found, unexpectedly, that pyrrolecarboxylic acid derivatives and indolecarboxylic acid derivatives with certain combinations of substituents have an improved inhibitory effect and less cytotoxicity than the known derivatives and therefore can be utilized better than the latter for preventing and/or treating disorders caused or partly caused by an increased activity of the enzyme phospholipase $A_2$, such as, for example, inflammations, allergies, asthma, psoriasis and endotoxic shock.

It is known that there are several different phospholipases $A_2$ (Connolly and Robinson, Drug News & Perspectives 1993, 6, 584–590). The key enzyme in the biosynthesis of said pathophysiologically significant lipid mediators is so-called cytosolic phospholipase $A_2$ (cPLA$_2$) (Clark et al., J. Lipid Mediators Cell Signalling 1995, 12, 83–117). The compounds according to the invention inhibit in particular this cPLA$_2$.

The present invention thus relates to substituted pyrrole compounds and substituted indole compounds of the general formulae I and II:

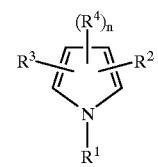

I

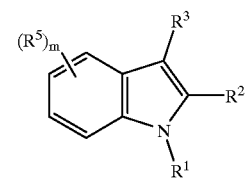

II in which
$R^1$ is a radical —$Y^1$—Ar—$Y^2$—$Y^3$ where $Y^1$ is a $C_1$–$C_{12}$-alkyl, $C_2$–$C_{12}$-alkenyl, $C_1$–$C_{12}$-alkyloxy or $C_2$–$C_{12}$-alkenyloxy radical which can optionally be interrupted by one or more oxygen atoms, Ar is an aryl group which may optionally be substituted by 1 to 3 substituents selected from the group $R^6$, $R^7$ and $R^8$, $Y^2$ is a $C_1$–$C_{12}$-alkyl, $C_2$–$C_{12}$-alkenyl, $C_1$–$C_{12}$-alkyloxy or $C_2$–$C_{12}$-alkenyloxy radical which can optionally be interrupted by one or more oxygen atoms, and $Y^3$ is —$COOR^{17}$, —$CONR^{17}R^{17}$, —$CONHCOR^{19}$, —$CONHS(O)_2R^{19}$, —$CONHNHS(O)_2R^{19}$, or —Tz where Tz is 1H— or 2H-tetrazol-5-yl;

$R^2$ is —$COOR^{17}$, —$Y^4$—$COOR^{17}$, —$CONR^{17}R^{17}$, —$Y^4$—$CONR^{17}R^{17}$, —$CONHCOR^{19}$, —$Y^4$—$CONHCOR^{19}$, —$CONHS(O)_2R^{19}$, —$Y^4$—$CONHS(O)_2R^{19}$, —$CONHNHS(O)_2R^{19}$, —$Y^4$—$CONHNHS(O)_2R^{19}$, —Tz or —$Y^4$—Tz where $Y^4$ is a $C_1$–$C_8$-alkyl or $C_2$–$C_8$-alkenyl group which can optionally be interrupted by an oxygen atom, and Tz is 1H— or 2H-tetrazol-5-yl;

$R^3$ is —CO—$R^9$ where $R^9$ is —$Y^5$, -aryl or —$Y^5$-aryl, where $Y^5$ is a $C_1$–$C_{19}$-alkyl or $C_2$–$C_{19}$-alkenyl or -alkynyl group which can optionally be interrupted by one or more oxygen atoms, and aryl is an aryl group which is optionally substituted by 1 to 3 substituents selected from the group of $R^{10}$, $R^{11}$ and $R^{12}$;

each $R^4$ radical is, independently of the others, a. hydrogen atom, a halogen atom, —$CF_3$, —$Y^6$, -aryl or —$Y^6$-aryl, where $Y^6$ is a $C_1$–$C_8$-alkyl or $C_2$–$C_8$-alkenyl or -alkynyl group which can optionally be interrupted by one or more oxygen atoms, and aryl is an aryl group which is optionally substituted by 1 to 3 substituents selected from the group of $R^{13}$, $R^{14}$ and $R^{15}$, and n is the number 2; and where two $Y^6$ radicals can, if they are two adjacent alkyl radicals, form together with the carbon atom to which they are bonded a 5–8-membered ring which may optionally be substituted by 1 to 2 $C_1$–$C_4$-alkyl groups; each $R^5$ radical is, independently of the others, a hydrogen atom or $R^{16}$, and m is the number 4; $R^6$, $R^7$, $R^8$, $R^{10}$, $R^{11}$, $R^{12}$, $R^{13}$, $R^{14}$, $R^{15}$ and $R^{16}$ are selected independently of one another from:

(1) $C_1$–$C_{20}$-alkyl group which can optionally be interrupted by an oxygen heteroatom;
(2) $C_2$–$C_{20}$-alkenyl group which can optionally be interrupted by an oxygen heteroatom;
(3) $C_2$–$C_{20}$-alkynyl group which can optionally be interrupted by an oxygen heteroatom;
(4) halogen;
(5) —$CF_3$;
(6) perhalo-$C_1$–$C_6$-alkenyl;
(7) —CN;
(8) —$NO_2$;
(9) —$OR^{17}$;
(10) —$SR^{17}$;
(11) —$COOR^{17}$;
(12) —$COR^{18}$;
(13) —$COCH_2OH$;
(14) —$NHCOR^{17}$;
(15) —$NR^{17}R^{17}$;
(16) —$NHS(O)_2R^{17}$;
(17) —$SOR^{17}$;
(18) —$S(O)_2R^{17}$;
(19) —$CONR^{17}R^{17}$;
(20) —$SO_2NR^{17}R^{17}$;
(21) —$OOCR^{18}$;
(22) —$OOCNR^{17}R^{17}$;
(23) —$OOCOR^{17}$;
(24) —$(CH_2)_rOR^{23}$;
(25) —$(CH_2)_rSR^{23}$;
(26) $(CH_2)_rNHR^{23}$;
(27) $(CH_2)_sR^{20}$;

$R^{17}$ is in each case, independently of one another, hydrogen, a $C_1$–$C_{20}$-alkyl or $C_2$–$C_{19}$-alkenyl or -alkynyl group which can optionally be interrupted by an oxygenheteroatom, or —$(CH_2)_rR^{20}$;

$R^{18}$ is in each case, independently of one another, $R^{17}$, —$CF_3$, —$(CH_2)_uCOOH$ or —$(CH_2)_uCOOR^{21}$;

$R^{19}$ is in each case, independently of one another, $R^{17}$ or —$CF_3$;

$R^{20}$ is in each case, independently of one another, aryl substituted by one or two $R^{22}$ groups;

$R^{21}$ is in each case, independently of one another, $C_1$–$C_6$-alkyl, benzyl or phenyl;

$R^{22}$ is in each case, independently of one another, hydrogen, halogen, $C_1$–$C_{12}$-alkyl, $C_1$–$C_{12}$-alkoxy, $C_1$–$C_{12}$-alkylthio, $C_1$–$C_{12}$-alkylsulfonyl, $C_1$–$C_{12}$-alkylcarbonyl, —$CF_3$, —CN or —$NO_2$;

$R^{23}$ is in each case, independently of one another, hydrogen or —$COR^{21}$; r is 1 to 20;

s and t are in each case, independently of one another, 0 to 12;

u is 0 to 4;

and the pharmaceutically suitable salts and esters thereof.

It has been found according to the invention that an improved inhibitory effect and/or less cytotoxicity of the compounds can be obtained by the specific substitution of the nitrogen atom.

The pharmaceutically suitable salts can be base addition salts. These include salts of the compounds with inorganic bases such as alkali metal hydroxides, alkaline earth metal hydroxides or with organic bases such as mono-, di- or triethanolamine. Acid addition salts are also embraced.

The pharmaceutically suitable esters of the compounds include, in particular, esters which readily undergo physiological hydrolysis, for example alkyl, pivaloyloxymethyl, acetoxymethyl, phthalidyl, indanyl and methoxymethyl esters.

The term "alkyl" used herein embraces straight-chain, branched or cyclic alkyl groups such as methyl, ethyl, n- and iso-propyl, n-, iso- or t-butyl, n-pentyl, neopentyl, n-undecyl, n-dodecyl, n-pentadecyl, n-hexadecyl, n-heptadecyl, n-octadecyl, cyclopentyl, cyclohexyl, cyclododecyl etc.

The term "alkenyl" embraces straight-chain, branched or cyclic alkenyl groups such as ethenyl, propenyl, butenyl, decenyl, heptadecenyl, cyclo-pentenyl, cyclohexenyl, etc.

The term "alkynyl" embraces straight-chain or branched alkynyl groups such as ethynyl, propynyl, butynyl, decynyl, heptadecynyl, etc.

The term "aryl" embraces aromatic hydrocarbons with 5 to 14 carbon atoms which may contain a heteroatom such as oxygen, sulfur or nitrogen. Phenyl, naphthyl and pyridyl groups are particularly preferred.

The term "halogen atom" embraces fluorine, chlorine, bromine or iodine atom, with a fluorine or chlorine atom being particularly preferred.

A particularly suitable $R^2$ radical for the present invention is the corresponding radical of formic acid, acetic acid, 3-propionic acid, 4-butyric acid, 3-α-methylpropionic acid and 3-acrylic acid. Radicals of formic acid, acetic acid, 3-propionic acid, 3-α-methylpropionic acid and 4-butyric acid are preferred.

Particularly suitable as $R^3$ radical are ($C_{1-19}$-alkyl-, -alkenyl- or -alkynyl-)carbonyl groups which may optionally be interrupted by several, in particular by one oxygen atom. $R^3$ may moreover be substituted by an aryl group. This aryl group may optionally comprise one or more, in particular one or two, substituents. Substituents suitable according to the invention are radicals from the group of halogen atom, nitro, trifluoromethyl, $C_{4-12}$-alkyl, $C_{1-12}$-alkoxy and hydroxyl group. ($C_{7-17}$-Alkyl)carbonyl and aryl($C_{1-17}$-alkyl) carbonyl groups are particularly preferred.

The groups which may be particularly mentioned for the $R^3$ substituents are octanoyl, nonanoyl, decanoyl, dodecanoyl, hexadecanoyl and octadecanoyl.

Particularly suitable for the $R^4$ radicals are a hydrogen atom, a $C_{1-8}$-alkyl or $C_{2-8}$-alkenyl or $C_{2-8}$-alkynyl group which may optionally be interrupted by one or more oxygen atoms, an optionally substituted aryl group or a $C_{1-8}$-alkyl, $C_{2-8}$-alkenyl or $C_{2-8}$-alkynyl group substituted by an aryl radical.

Both the aryl group for $R^4$, and the aryl group Ar which may be a substituent of the alkyl, alkenyl or alkynyl group, can be substituted. Preference is given in this connection to one or two substituents selected from $C_{1-4}$-alkyl, in particular methyl, $C_{1-4}$-alkoxy, in particular methoxy, trifluoromethyl, hydroxyl, amino, N,N-di-$C_{1-4}$-alkylamino, in particular N,N-dimethylamino, amino-$C_{1-4}$-alkyl, in particular aminomethyl, cyano, carbamoyl, N,N-di-$C_{1-4}$-alkylcarbamoyl, in particular N,N-dimethylcarbamoyl, carboxyl, $C_{1-4}$-alkylsulfonyl, in particular methylsulfonyl, group and halogen atom.

Particular mention may be made for the $R^4$ radicals of hydrogen, methyl, ethyl, propyl, butyl, pentyl, neopentyl, hexyl, heptyl, octyl, 3-phenylpropyl, phenyl and benzyl.

Particularly preferred compounds are those in which the $R^4$ radicals are each, independently of one another, a hydrogen atom, a $C_{1-5}$-alkyl radical, a benzyl or phenyl group.

The radicals preferred according to the invention for the $R^2$ and $R^3$ radicals are those which, if present, contain saturated alkyl radicals without oxygen atoms.

The invention particularly embraces compounds of the general formula I':

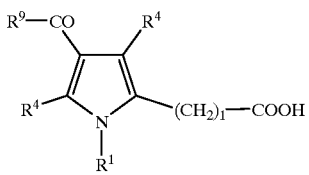

I' in which $R^9$ is preferably a $C_{7-17}$-alkyl or aryl($C_{1-17}$-alkyl) group with optionally substituted aryl radical; and the $R^4$ radicals are each, independently of one another, selected from the group consisting of a hydrogen atom, a methyl, phenyl and benzyl group; and 1 is an integer from 0 to 3.

Particularly preferred compounds of the formula I' are those in which 1 is the number 1 or 2, $R^9$—CO— is a ($C_{7-17}$-alkyl)carbonyl or aryl($C_{1-17}$-alkyl)carbonyl group and the $R^4$ radicals are each, independently of one another, a hydrogen atom or a methyl or benzyl group. The compounds particularly preferred in this connection are those in which 1 is the number 1 or 2, $R^9$—CO is a ($C_{7-17}$-alkyl) carbonyl group and the $R^4$ radicals are each a hydrogen atom or a methyl group.

Further preferred compounds of the formula I' are those in which 1 is the number 1 or 2, $R^9$—CO— is a dodecanoyl group, and the $R^4$ radicals are each, independently of one another, a hydrogen atom or a methyl or benzyl group.

Particularly preferred according to the invention is 3,5-dimethyl-4-dodecanoylpyrrol-2-ylacetic acid which has a —$Y^1$—Ar—$Y^2$—$Y^3$ radical as $R^1$ radical.

The $Y^1$ radical is preferably a $C_1$–$C_4$-alkyl radical and particularly preferably a methylene group. The Ar radical is preferably an unsubstituted phenylene group and the $Y^2$ radical is preferably a $C_1$–$C_6$-alkyl or $C_2$–$C_6$-alkenyl radical, particularly preferably an ethenylene or ethylene group. The $Y^2$ radical is preferably in the meta or para position to the $Y^1$ radical. The $Y^3$ radical is preferably a carboxyl group.

The substituted indole compounds of the general formula II preferably have formula II'

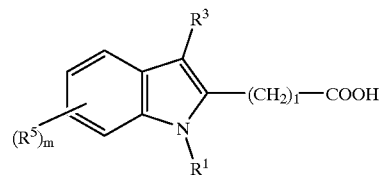

II'

The preferred meanings of the $R^3$ radical are as explained above in connection with formula I and I'. Index 1 in formula II' preferably has the value 0.

The $R^1$ radical in formula II or II' is particularly preferably a $Y^1$—Ar—$Y^2$-COOH radical. The $Y^1$ radical is in this case preferably a $C_1$–$C_4$-alkyl or alkoxy radical and particularly preferably a methylene, ethylene, methoxy or ethoxy group. The Ar radical is preferably an unsubstituted phenylene group. The $Y^2$ radical is preferably a $C_{1-4}$-alkyl-, $C_{2-4}$-alkenyl or $C_{1-4}$-alkoxy radical, with methylene, methoxy, ethylene and ethenylene groups being preferred. The $Y^2$ radical is preferably in the meta or para position to the $Y^1$ radical.

All $R^5$ radicals are preferably hydrogen atoms or one $R^5$ radical is a halogen atom, in particular 4-or 5-chlorine atom, or an alkoxy, in particular 5-methoxy, group.

If the compounds of the formula I or II also contain amino or dialkylamino groups, the present invention also embraces the salts thereof, in particular the hydrochlorides thereof.

The compounds according to the invention have proved to be potent phospholipase $A_2$ inhibitors. The compounds can therefore be used as pharmaceuticals for preventing and/or treating disorders caused or partly caused by products or secondary products of this enzyme, such as, for example, for treating rheumatic disorders and for preventing and treating disorders induced by allergies. The compounds according to the invention thus represent, inter alia, effective analgesic, antiinflammatory, antipyretic, antiallergic and bronchospasmolytic agents and can be used for the prophylaxis of thrombosis and for the prophylaxis of anaphylactic shock, and for treating dermatological disorders such as psoriasis, urticaria, acute and chronic exanthemas of allergic and nonallergic origin.

The compounds according to the invention can be administered either as single therapeutic agents or as mixtures with other therapeutic agents. They can be administered alone, but they are in general administered in the form of pharmaceutical compositions, i.e. as mixtures of the agents with suitable pharmaceutical carriers or diluents. The compounds or compositions can be administered orally, parenterally, by inhalation or topically (including dermally, transdermally, buccally and sublingually).

The nature of the pharmaceutical composition and of the pharmaceutical carrier or diluent depends on the required mode of administration. Oral compositions can be, for example, in the form of tablets or capsules, also in slow-release form, and may comprise conventional excipients such as binders (for example gum acacia, gelatin, sorbitol, tragacanth or polyvinyl-pyrrolidone), bulking agents (for example lactose, sugars, cornstarch, calcium phosphate, sorbitol or glycine), lubricants (for example magnesium stearate, talc, polyethylene glycol or silicon dioxide), disintegrants (for example starch) or wetting agents (for example sodium lauryl sulfate). Oral liquid products may be in the form of aqueous or oily suspensions, solutions, emulsions, syrups, elixirs or sprays etc., and may be in the form of a dry powder for reconstitution with water or another suitable carrier. Liquid products of these types may contain conventional additives, for example suspending agents, flavorings, diluents or emulsifiers. Solutions or suspensions with conventional pharmaceutical carriers can be employed for parenteral administration. For administration by inhalation, the compounds can be in the form of aqueous or partly aqueous solution which can be used in the form of an aerosol. Compositions for topical application may be, for example, in the form of pharmaceutically suitable dusting powders, lotions, ointments, creams, gels or therapeutic systems which contain therapeutically effective amounts of the compounds according to the invention.

The necessary dose depends on the form of the pharmaceutical composition used, on the mode of use, the severity of the symptoms and the specific subject (human or animal) which is being treated. The treatment will normally be started with a dose which is below the optimal dose. The dose will then be increased until the effect optimal for the given conditions is achieved. It will in general be best to administer the compounds according to the invention in concentrations with which effective actions can be achieved without harmful or disadvantageous actions occurring. They may be administered in a single dose or in a plurality of doses.

The efficacy of the compounds according to the invention can be determined on the basis of the inhibition of phospholipase $A_2$. For this purpose, the phospholipaase $A_2$ in intact bovine platelets is stimulated with calcium ionophore A23187, and thus the release of arachidonic acid from the membrane phospholipids is induced. In order to prevent metabolism of the enzyme product arachidonic acid by the cyclooxygenase pathway and the 12-lipoxygenase pathway, in this case the dual cyclooxygenase/12-lipoxygenase inhibitor 5,8,11,14-eicosatetraynoic acid is added. After purification by solid phase extraction, the released arachidonic acid is determined by reversed phase HPLC with UV detection. The inhibition of the enzyme by a test substance is evident from the ratio between the amounts of arachidonic acid formed in the presence and in the absence of the test substance. Further details of the test system are to be found in Example 15.

The present invention also embraces processes for preparing the substituted pyrrole compounds and the substituted indole compounds.

The compounds according to the invention can be prepared by the following methods.

Method 1

Suitable starting compounds for preparing compounds according to the invention are the acyl-pyrrolecarboxylic esters III and the 3-acyl-indolecarboxylic esters VI. These esters are alkylated on the indolenitrogen to give the compounds IV and VII respectively. The N-alkylation takes place, for example, in a conventional way using the appropriate alkyl halides Br—$Y^1$-aryl—$Y^2$—$COOR^{21}$ in the presence of a base, for example alkali metal alcoholate, such as potassium t-butoxide, in an inert solvent such as DMSO or the like. The N-alkylation can also be carried out heterogeneously using phase-transfer catalysts in an organic solvent such as ether with the addition of powdered alkali metal hydroxide, such as sodium hydroxide. The carboxylic acids V and VIII according to the invention are obtained from IV and VII, respectively, by ester cleavage. The ester cleavage can take place by hydrolysis, for example with alcoholic potassium hydroxide solution, or in the case of the benzyl esters also by hydrogenolysis, for example in THF with hydrogen in the presence of Pd/C. The latter method is indicated in particular when other hydrolysis-sensitive functional groups, besides the ester groups, are present in the compounds or when only one of the two ester groups is to be cleaved.

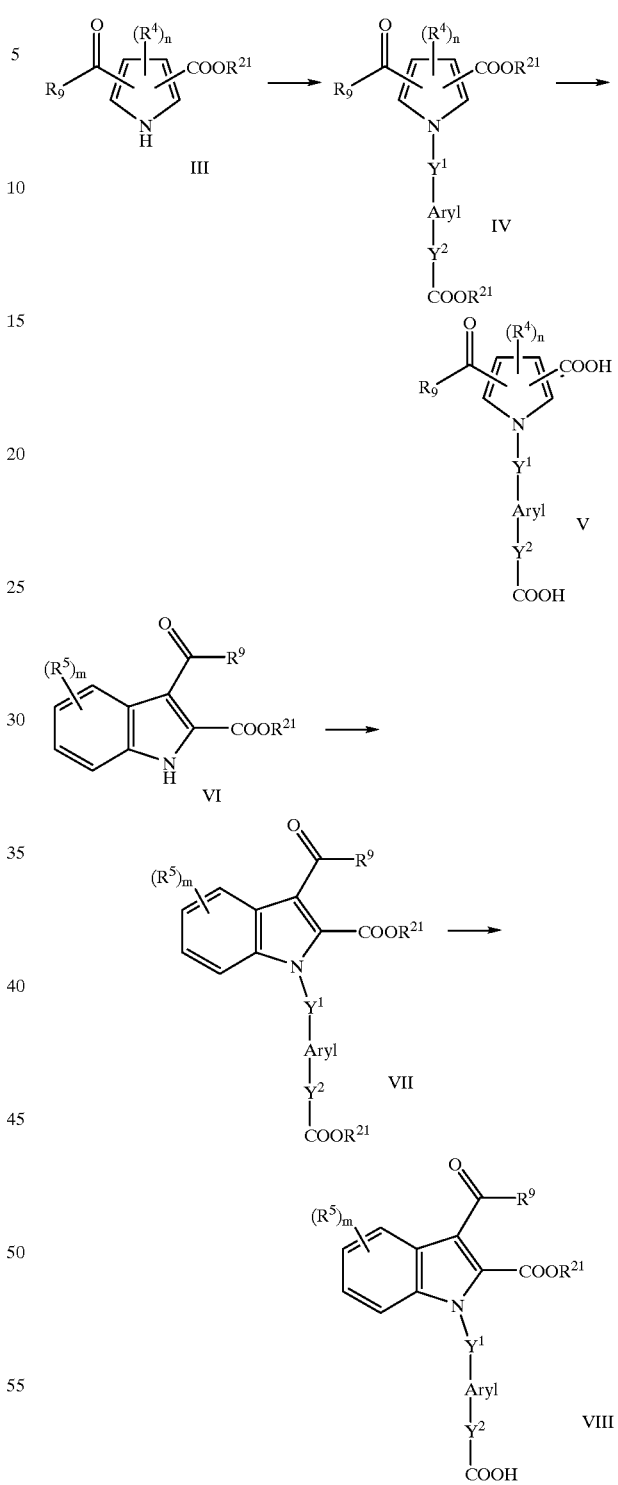

Method 2

An alternative possibility for preparing acylpyrrolecarboxylic acids according to the invention is by Method 2. This entails initial N-alkylation of the acylpyrroles IX as in Method 1. The carboxylic acid residue is then introduced, for example by reaction with chloroformic esters, diazoacetic esters, acrylic acid or acrylic esters using suitable catalysts such as, for example, copper for reaction with diazoacetic esters and $AlCl_3$ or $BF_3$ for reaction with chloroformic esters, acrylic acid or acrylic esters. The resulting compounds can finally be hydrolyzed where appropriate as described under Method 1 to give the carboxylic acids XI and XII.

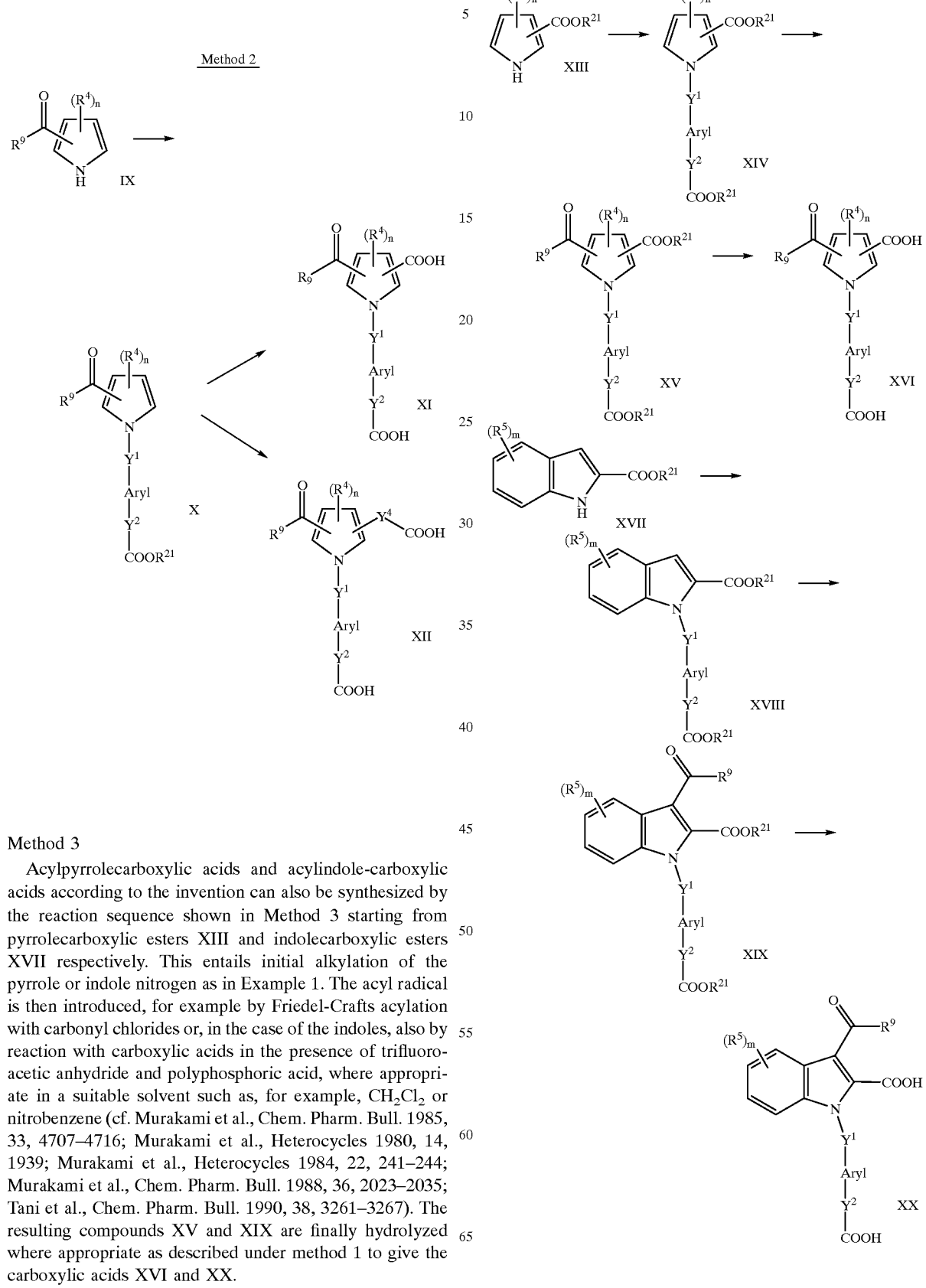

Method 3

Acylpyrrolecarboxylic acids and acylindole-carboxylic acids according to the invention can also be synthesized by the reaction sequence shown in Method 3 starting from pyrrolecarboxylic esters XIII and indolecarboxylic esters XVII respectively. This entails initial alkylation of the pyrrole or indole nitrogen as in Example 1. The acyl radical is then introduced, for example by Friedel-Crafts acylation with carbonyl chlorides or, in the case of the indoles, also by reaction with carboxylic acids in the presence of trifluoroacetic anhydride and polyphosphoric acid, where appropriate in a suitable solvent such as, for example, $CH_2Cl_2$ or nitrobenzene (cf. Murakami et al., Chem. Pharm. Bull. 1985, 33, 4707–4716; Murakami et al., Heterocycles 1980, 14, 1939; Murakami et al., Heterocycles 1984, 22, 241–244; Murakami et al., Chem. Pharm. Bull. 1988, 36, 2023–2035; Tani et al., Chem. Pharm. Bull. 1990, 38, 3261–3267). The resulting compounds XV and XIX are finally hydrolyzed where appropriate as described under method 1 to give the carboxylic acids XVI and XX.

The —COOH and —COOR$^{21}$ groups occurring in the intermediate and final products in Methods 1 to 3 can be converted independently of one another, by means of methods described in the literature, into —CONR$^{17}$R$^{17}$, —CONHCOR$^{19}$, —CONHS(O)$_2$R$^{19}$, —CONHNHS(O)$_2$R$^{19}$ and 1H- and 2H-tetrazol-5-yl.

Representative Compounds

Tables 1 and 2 show representative compounds of the invention.

TABLE 1

| Example No. | R$^1$ | R$^2$ | R$^4$/R$^4$ | R$^9$ |
|---|---|---|---|---|
| 1 | —CH$_2$-(4-C$_6$H$_4$)-CH$_2$CH$_2$-COOH | —COOH | H/H | —C$_{11}$H$_{23}$ |
| 2 | —CH$_2$-(3-C$_6$H$_4$)-CH=CH-COOH | —CH$_2$COOH | CH$_3$/CH$_3$ | —C$_{11}$H$_{23}$ |
| 3 | —CH$_2$-(3-C$_6$H$_4$)-CH$_2$CH$_2$-COOH | —CH$_2$COOH | CH$_3$/CH$_3$ | —C$_{11}$H$_{23}$ |
| 4 | —CH$_2$-(4-C$_6$H$_4$)-CH=CH-COOH | —CH$_2$COOH | CH$_3$/CH$_3$ | —C$_{11}$H$_{23}$ |
| 5 | —CH$_2$-(4-C$_6$H$_4$)-CH$_2$CH$_2$-COOH | —CH$_2$COOH | CH$_3$/CH$_3$ | —C$_{11}$H$_{23}$ |
| 6 | —CH$_2$-(4-C$_6$H$_4$)-CH=CH-COOH | —CH$_2$CH$_2$COOH | CH$_3$/CH$_3$ | —C$_{17}$H$_{35}$ |
| 7 | —CH$_2$-(4-C$_6$H$_4$)-CH=CH-COOH | —CH$_2$CH$_2$COOH | CH$_3$/CH$_3$ | —C$_{17}$H$_{35}$ |

TABLE 2

| Example No. | R¹ |
|---|---|
| 8 | —CH₂—[phenyl]—CH=CH—COOH |
| 9 | —CH₂—[phenyl]—CH₂CH₂—COOH |
| 10 | —CH₂—[phenyl]—CH=CH—COOH |
| 11 | —CH₂—[phenyl]—CH₂CH₂—COOH |
| 12 | —CH₂—[phenyl]—O—CH₂—COOH |
| 13 | —(CH₂)₂O—[phenyl]—COOH |
| 14 | —(CH₂)₂O—[phenyl]—CH₂—COOH |

The following examples illustrate the invention.

The batches were carried out with exclusion of atmospheric oxygen. Silicagel 60 (70–230 mesh ASTM) supplied by Merck, Darmstadt, was used for column chromatography (CC); for loading on the columns, the substances were dissolved in solvents whose solvent strength was less than the solvent strength of the eluant stated in each case (normally toluene, CHCl₃ or CH₂Cl₂ or mixtures of these solvents with petroleum ether). All stated temperatures are uncorrected. For recording the mass spectra, ionization was either by electron impact (EI) or chemically with CH₄ gas or CH₅⁺ ions (CI). The NMR spectra are 400 MHz spectra recorded with tetramethylsilane (TMS) as internal standard.

EXAMPLE 1

1-[4-(2-Carboxyethyl)benzyl]-4-dodecanoylpyrrole-2-carboxylic acid

A. Methyl 4-dodecanoylpyrrole-2-carboxylate 1.46 g (11 mmol) of AlCl₃ are added to a solution of 1.25 g (10 mmol) of methyl pyrrole-2-carboxylate and 2.63 g (12 mmol) of dodecanoyl chloride in 30 ml of absol. CH₂Cl₂ and then stirred for 24 h. Addition of water is followed by extraction with ether. The organic phase is dried over Na₂SO₄, and the solvent is distilled off. The product is isolated by CC (silica gel, 1. petroleum ether/ethyl acetate 9+1, 2. CHCl₃, 3. petroleum ether/ethyl acetate 8+2) and precipitated from petroleum ether.

Yield: 1.2 g (39%). Melting point: 92–94° C. $C_{18}H_{29}NO_3$ (307.4). MS (CI): m/z (rel.int.)=308 (100%), 277 (5%), 250 (7%).

$^1$H-NMR (CDCl₃): δ (ppm)=0.88 (t, J–7 Hz, 3H, CH₃), 1.14–1.39 (m, 16H, (CH₂)₈), 1.70 (quint, J=7 Hz, 2H, C$\underline{H}$₂CH₂CO), 2.75 (t, J=7 Hz, 2H, CH₂C$\underline{H}$₂CO), 3.89 (s, 3H, OCH₃), 7.29 (S, 1H, aromat. H), 7.54 (s, 1H, aromat. H), 9.40 (broad, 1H, NH)

B. Methyl (E)-4-dodecanoyl-1-{4-[2-(ethoxycarbonyl)-ethenyl]benzyl}pyrrole-2-carboxylate A mixture of 307 mg (1 mmol) of methyl 4-dodecanoylpyrrole-2-carboxylate, 124 mg (1.1 mmol) of potassium t-butoxide and 3 ml of absol. DMSO is stirred in an oil bath at 110° C. for 5 min. Then 296 mg (1.1 mmol) of ethyl (E)-4-(bromomethyl)cinnamate (Wang J.-Y, Jun Y.-F. CA 62:1592a) are added, and the mixture is heated at the same temperature for a further 10 min. After cooling, water and NaCl are added and ether extraction is carried out. The organic phase is dried over Na₂SO₄, the solvent is distilled off, and the product is isolated by CC (silica gel, petroleum ether/ethyl acetate 9+1). The product fractions are concentrated; the remaining oil crystallizes after some time.

Yield: 252 mg (51%). Melting point: 79–80° C. $C_{30}H_{41}NO_5$ (495.7). MS (EI): m/z (rel.int.)=495 (12%), 355 (100%), 189 (60%), 115 (29%)

$^1$H-NMR (CDCl₃): δ (ppm)=0.88 (t, J=7 Hz, 3H, CH₃), 1.17–1.39 (m, 16H, (CH₂)₈), 1.33 (t, J–7 Hz, 3H, OCH₂C$\underline{H}$₃), 1.69 (quint. J=7 Hz, 2H, C$\underline{H}$₂CH₂O), 2.73 (t, J=7 Hz, 2H, CH₂C$\underline{H}$₂CO), 3.80 (s, 3H, OCH₃), 4.26 (q, J=7 Hz, 2H, OC$\underline{H}$₂CH₃), 5.57 (s, 2H, NCH₂), 6.41 (d, J=16 Hz, 1H, CH=C$\underline{H}$CO), 7.14 (d, J=8 Hz, 2H, aromat. H), 7.38 (d, J=2 Hz, 1H, aromat. H), 7.48 (d, J=8.Hz, 2H, aromat. H), 7.48 (d, J=2 Hz, 1H, aromat. H), 7.64 (d, J=16 Hz, 1H, C$\underline{H}$=CHCO)

C. 1-[4-(2-Carboxyethyl)benzyl]-4-dodecanoylpyrrole-2-carboxylic acid 50 mg (0.1 mmol) of methyl (E)-4-dodecanoyl-1-{4-[2-(ethoxycarbonyl)ethenyl]benzyl}pyrrole-2-carboxylate are dissolved in 5 ml of THF. After addition of a spatula tip of Pd/C, hydrogenation is carried out with vigorous stirring at room temperature under a hydrogen atmosphere produced using a hydrogen-filled balloon fitted onto the reaction flask for 4 h. Addition of kieselguhr is followed by filtration, the solvent is distilled off, the residue is mixed with 12 ml of ethanol and 4 ml of 10% strength aqueous KOH, and the resulting mixture is boiled under reflux for 1 h. Cooling is followed by dilution with water, acidification with dilute HCl and extraction with ether. The organic phase is washed with dilute HCl, dried over Na₂SO₄ and concentrated. The product is precipitated from petroleum ether.

Yield: 26 mg (57%). Melting point: 131–132° C. $C_{27}H_{37}NO_5$ (455.6).

$^1$H-NMR (CDCl₃): δ (ppm)=0.88 (t, J=7 Hz, 3H, CH₃), 1.13–1.32 (m, 16H, (CH₂)₈), 1.54 (quint, J=7 Hz, 2H, C H₂CH₂CO), 2.42 (t, J=7 Hz, 2H, CH₂), 2.68 (t, J=7 Hz, 2H, CH₂), 2.91 (t, J=7 Hz, 2H, CH₂), 5.44 (s, 2H, NCH₂), 6.74 (d, J=2 Hz, 1H, aromat. H), 6.91 (d, J=8 Hz, 2H, aromat. H), 6.96 (d, J=2 Hz, 1H, aromat. H), 7.12 (d, J=8 Hz, 2H, aromat. H)

EXAMPLE 2

(E)-3-{[2-(Carboxymethyl)-4-dodecanoyl-3,5-dimethyl-pyrrol-1-yl]methyl}cinnamic acid A. Ethyl dodecanoyl-3, 5-dimethylpyrrole-2-carboxylate 1.46 g (11 mmol) of AlCl₃ were added to a solution of 1.67 g (10 mmol) of ethyl 3,5-dimethylpyrrole-2-carboxylate a 2.63 g (12 mmol) of dodecanoyl chloride in 30 ml of absol. Dichloromethane and then stirred for 24 h. Addition of water and dilute HCl is followed by extraction twice with CH₂Cl₂. The organic phases are washed with dilute NaOH, dried over Na₂SO₄ and concentrated. The product is recrystallized from isopropanol.

Yield: 1.45 g (41%). Melting point: 85–87° C. C₂₁H₃₅NO₃ (349.5). MS (EI): m/z (rel.int.)=349 (12%), 209 (86%), 194 (100%), 148 (97%).

¹H-NMR (CDCl₃): δ (ppm)=0.88 (t, J=7 Hz, 3H, CH₃), 1.18–1.42 (m, 16H, (CH₂)₈), 1.37 (t, J=7 Hz, 3H, OCH₂CH₃), 1.68 (quint, J=7 Hz, 2H, CH₂CH₂CO), 2.51 (s, 3H, PyrCH₃), 2.59 (s, 3H, PyrCH₃), 2.72 (t, J=7 Hz, 2H, CH₂CH₂CO), 4.33 (q, J=7 Hz, 2H, OCH₂CH₃), 8.87 (broad, 1H, NH)

B. 3-Dodecanoyl-2,4-dimethylpyrrole

A mixture of 1.40 g (4 mmol) of ethyl 4-dodecanoyl-3,5-dimethylpyrrole-2-carboxylate, 30 ml of ethanol and 10 ml of 20% strength aqueous KOH solution is boiled for 2 hours. Water is then added, followed by acidification with 10% strength HCl and extraction with CHCl₃ twice. The solvent is distilled off and the residue is heated in an oil bath at 160–170° C. under water pump vacuum for 20 minutes. The product is isolated by CC (neutral alumina, act. I, petroleum ether/ethyl acetate 9+1) and precipitated from petroleum ether.

Yield: 0.85 g (76%). Melting point: 59–60° C. C₁₈H₃₃NO (279.5). MS (El): m/z (rel.int.)=277 (12%), 137 (44%), 122 (100%).

¹H-NMR (CDCl₃): δ (ppm)=0.88 (t, J=7 Hz, 3H, CH₃), 1.18–1.42 (m, 16H, (CH₂)₈), 1.68 (quint, J=7 Hz, 2H, CH₂CH₂CO, 2.28 (s, 3H, PyrCH₃), 2.50 (s, 3H, PyrCH₃), 2.71 (t, J=7 Hz, 2H, CH₂CH₂CO), 6.36 (s, 1H, aromat. H), 7.92 (broad, 1H, NH)

C. (E)-3-[(3-Dodecanoyl-2,4-dimethylpyrrol-1-yl)-methyl]cinnamate

A mixture of 277 mmg (1 mmol) 3-dodecanoyl-2,4-dimethylpyrrole, 296 mg (1.1 mmol) of ethyl (E)-3-(bromomethyl)cinnamate (Wang J.-Y, Jun Y.-F., CA 64:1592a), 35 mg (0.11 mmol) of tetrabutylammonium bromide, 200 mg of powdered NaOH, 10 ml of ether, 5 ml of CH₂Cl₂ and 2 drops of water is gently boiled with vigorous stirring for 3 h. The mixture is then filtered and the residue on the filter is washed with CH₂Cl₂. The filtrates are dried over Na₂SO₄, the solvent is distilled off, and the resulting product is isolated by CC (silica gel, petroleum ether/ethyl acetate 9+1). The product fractions are concentrated; the remaining oil crystallizes after some time.

Yield: 272 mg (58%). Melting point: 58–60° C. C₃₀H₄₃NO₃ (465.7). MS (EI): m/z (rel.int.)=465 (23%), 310 (100%), 189 (38%), 122 (15%).

¹H-NMR (CDCl₃): δ (ppm)=0.88 (t, J=7 Hz, 3H, CH₃), 1.20–1.41 (m, 16H, (CH₂)₈), 1.34 (t,J=7 Hz, 3H, OCH₂CH₃), 1.69 (quint, J=7 Hz, 2H, CH₂CH₂CO), 2.28 (s, 3H, PyrCH₃), 2.41 (s, 3H, PyrCH₃), 2.73 (t, J=7 Hz, 2H, CH₂CH₂CO), 4.26 (q, J=7 Hz, 2H, OCH₂CH₃), 4.99 (s, 2H, NCH₂), 6.35 (s, 1H, aromat. H), 6.39 (d, J=16 Hz, 1H, CH=CHCO), 7.01 (d, J=8 Hz, 1H, aromat. H), 7.15 (s, 1H, aromat. H), 7.34 (t, J=8 Hz, 1H, aromat. H), 7.45 (d, J=8 Hz, 1H, aromat. H), 7.63 (d, J=16 Hz, 1H, CH=CHCO)

D. Ethyl (E)-3-({3-dodecanoyl-5-[(ethoxycarbonyl)-methyl]-2,4-dimethylpyrrol-1-yl}methyl)cinnamate 0.24 ml of ethyl diazoacetate is added in portions each of 0.08 ml over the course of 15 min to a stirred solution of 233 mg (0.5 mmol) of (E)-3-[(3-dodecanoyl-2,4-dimethylpyrrol-1-yl)methyl]cinnamate in 3 ml of absol. Toluene at a bath temperature of 115–120° C. After each of these additions of ethyl diazoacetate a spatula tip of copper powder is added. The mixture is then heated for a further 5 min. After cooling and after addition of a little petroleum ether, the complete mixture is loaded onto a silica gel column; elution takes place with petroleum ether/ethyl acetate 9+1. The product fractions are concentrated, leaving a waxy substance.

Yield: 119 mg (43%). C₃₄H₄₉NO₅ (551.8). MS (EI): m/z (rel.int.)=551 (47%), 478 (60%), 396 (100%), 338 (33%), 189 (72%).

¹H-NMR (CDCl₃): δ (ppm)=0.88 (t, J=7 Hz, 3H, CH₃), 1.18 (t, J=7 Hz, 3H, OCH₂CH₃), 1.18–1.41 (m, 16H, (CH₂)₈), 1.34 (t, J=7 Hz, 3H, OCH₂CH₃), 1.70 (quint, J=7 Hz, 2H, CH₂CH₂CO), 2.28 (s, 3H, PyrCH₃), 2.41 (s, 3H, PyrCH₃), 2.76 (t, J=7 Hz, 2H, CH₂CH₂CO), 3.45 (s, 2H, PyrCH₂COOC₂H₅), 4.01 (q, J=7 Hz, 2H, OCH₂CH₃), 4.26 (q, J=7 Hz, 2H, OCH₂CH₃), 5.16 (s, 2H, NCH₂), 6.38 (d, J=16 Hz, 1H, CH=CHCO), 6.85 (d, J=8 Hz, 1H, aromat. H), 7.02 (s, 1H, aromat. H), 7.32 (t, J=8 Hz, 1H, aromat. H), 7.43 (d, J=8 Hz, 1H, aromat. H), 7.61 (d, J=16 Hz, 1H, CH=CHCO)

E. (E)-3-{[2-(Carboxymethyl)-4-dodecanoyl-3,5-dimethyl-pyrrol-1-yl]methyl}cinnamic acid A mixture of 55 mg (0.1 mmol) of ethyl (E)-3-({3-dodecanoyl-5-[(ethoxycarbonyl)methyl]-2,4-dimethyl-pyrrol-1-yl}methyl)cinnamate, 12 ml of ethanol and 4 ml of 10% strength aqueous KOH solution is boiled for 1 h. Cooling is followed by dilution with water, acidification with dilute HCl and extraction with ether. The organic phase is washed with dilute HCl, dried over Na₂SO₄ and concentrated. The product is recrystallized from methanol/H₂O.

Yield: 14 mg (28%). Melting point: 133–135° C. C₃₀H₄₁NO₅ (495.7).

¹H-NMR (CDCl₃): δ (ppm)=0.88 (t, J=7 Hz, 3H, CH₃), 1.18–1.42 (m, 16H, (CH₂)₈), 1.71 (quint, J=7 Hz, 2H, CH₂CH₂CO), 2.32 (s, 3H, PyrCH₃), 2.41 (s, 3H, PyrCH₃), 2.78 (t, J=7 Hz, 2H, CH₂CH₂CO), 3.59 (s, 2H, PyrCH₂COOH), 5.11 (s, 2H, NCH₂), 6.24 (d, J=16 Hz, 1H, CH=CHCO), 6.81 (s, 1H, aromat. H), 7.18 (d, J=8 Hz, 1H, aromat. H), 7.37 (t, J=8 Hz, 1H, aromat. H), 7.48 (d, J=8 Hz, 1H, aromat. H), 7.52 (d, J=16 Hz, 1H, CH=CHCO)

EXAMPLE 3

3-(3-{[2-(Carboxymethyl)-4-dodecanoyl-3,5-dimethyl-pyrrol-1-yl]methyl}phenyl)propionic acid Preparation as in Example 1C using 55 mg (0.1 mmol) of ethyl (E)-3-({3-dodecanoyl-5-[(ethoxy-carbonyl)methyl]-2,4-dimethylpyrrol-1-yl}methyl)-cinnamate (Example 2D) in place of methyl (E)-4-dodecanoyl-1-{4-[2-(ethoxycarbonyl)ethenyl]benzyl}-pyrrole-2-carboxylate. The product is recrystallized from methanol/H₂O.

Yield: 24 mg (48%). Melting point: 94–96° C. C₃₀H₄₃NO₅ (497.7).

¹H-NMR (CDCl₃): δ (ppm)=0.88 (t, J=7 Hz, 3H, CH₃), 1.17–1.45 (m, 16H, (CH₂)₈), 1.69 (quint, J=7 Hz, 2H, CH₂CH₂O), 2.27 (s, 3H, PyrCH₃), 2.38 (s, 3H, PyrCH₃), 2.59

(t, J=7 Hz, 2H, CH$_2$), 2.75 (t, J=7 Hz, 2H, CH$_2$), 2.88 (t, J=7 Hz, 2H, CH$_2$), 3.52 (s, 2H, PyrC$\underline{H}_2$COOH), 5.08 (s, 2H, NCH$_2$), 6.69 (s, 1H, aromat. H), 6.77 (d, J=8 Hz, 1H, aromat. H), 7.07 (d, J=8 Hz, 1H, aromat. H), 7.22 (t, J=8 Hz, 1H, aromat. H)

EXAMPLE 4

(E)-4-{[2-(Carboxymethyl)-4-dodecanoyl-3,5-dimethyl-pyrrol-1-yl]methyl}cinnamic acid A. Ethyl (E) -4-[(3-dodecanoyl-2,4-dimethylpyrrol-1-yl)-methyl]cinnamate Preparation as in Example 2C with ethyl (E)-4-(bromomemthyl)cinnamate in place of ethyl (E)-3-(bromomethyl)cinnamate.

Yield: 267 mg (57%). Melting point: 57–59° C. C$_{30}$H$_{43}$NO$_3$ (465.7). MS (EI): m/z (rel.int.)=465 (3%), 310 (17%), 189 (20%), 122 (100%).

$^1$H-NMR (CDCl$_3$): δ (ppm)=0.88 (t, J=7 Hz, 3H, CH$_3$), 1.18–1.39 (m, 16H, (CH$_2$)$_8$), 1.34 (t, J=7 Hz, 3H, OCH$_2$C$\underline{H}_3$), 1.69 (quint, J=7 Hz, 2H, C$\underline{H}_2$CH$_2$CO), 2.28 (s, 3H, PyrCH$_3$), 2.40 (s, 3H, PyrCH$_3$), 2.72 (t, J=7 Hz, 2H, CH$_2$C$\underline{H}_2$CO), 4.26 (q, J=7 Hz, 2H, OC$\underline{H}_2$CH$_3$), 4.99 (s, 2H, NCH$_2$), 6.34 (s, 1H, aromat. H), 6.41 (d, J=16 Hz, 1H, CH=C$\underline{H}$CO), 7.01 (d, J=8 Hz, 2H, aromat. H), 7.47 (d, J=8 Hz, 2H, aromat. H), 7.64 (d, J=16 Hz, 1H, C$\underline{H}$=CHCO)

B. Ethyl (E)-4-({3-dodecanoyl-5-[ (ethoxycarbonyl)-methyl]-2,4-dimethylpyrrol-1-yl}methyl)cinnamate Preparation as in Example 2D with ethyl (E)-4-[(3-dodecanoyl-2,4-dimethylpyrrol-1-yl)methyl]cinnamate in place of ethyl (E)-3-[(3-dodecanoyl-2,4-dimethyl-pyrrol-1-yl)methyl]cinnamate.

Yield: 146 mg (53%). Melting point: 69–71° C. C$_{34}$H$_{49}$NO$_5$ (551.8). MS (EI): m/z (rel.int.)=551 (48%), 478 (48%), 396 (84%), 189 (100%), 115 (51%). $^1$H-NMR (CDCl$_3$): δ (ppm)=0.88 (t, J=7 Hz, 3H, CH$_3$), 1.18 (t, J=7 Hz, 3H, OCH$_2$C$\underline{H}_3$), 1.18–1.39 (m, 16H, (CH$_2$)$_8$), 1.34 (t, J=7 Hz, 3H, OCH$_2$C$\underline{H}_3$) 1.69 (quint, J=7 Hz, 2H, C$\underline{H}_2$CH$_2$CO), 2.27 (s, 3H, PyrCH$_3$), 2.40 (s, 3H, PyrCH$_3$), 2.75 (t, J=7 Hz, 2H, CH$_2$C$\underline{H}_2$CO), 3.45 (s, 2H, PyrC$\underline{H}_2$COOC$_2$H$_5$), 4.01 (q, J=7 Hz, 2H, OC$\underline{H}_2$CH$_3$), 4.26 (q, J=7 Hz, 2H, OC$\underline{H}_2$CH$_3$), 5.16 (s, 2H, NCH$_2$), 6.40 (d, J=16 Hz, 1H, CH=C$\underline{H}$CO), 6.88 (d, J=8 Hz, 2H, aromat. H), 7.45 (d, J=8 Hz, 2H, aromat. H), 7.63 (d, J=16 Hz, 1H, C$\underline{H}$=CHCO)

C. (E)-4-{[2-(Carboxymethyl)-4-dodecanoyl-3,5-dimethyl-pyrrol-1-yl]methyl}cinnamic acid Preparation as in Example 2E with ethyl (E)-4-({3-dodecanoyl-5-[(ethoxycarbonyl)methyl]-2,4-dimethyl-pyrrol-1-yl}methyl)cinnamate in place of ethyl (E)-3-({3-dodecanoyl-5-[(ethoxycarbonyl)methyl]-2,4-dimethyl-pyrrol-1-yl}methyl)cinnamate. The product is recrystallized from methanol.

Yield: 12 mg (53%). Melting point: 205–207° C. C$_{30}$H$_{41}$NO$_5$ (495.7).

$^1$H-NMR ([D6]-DMSO): δ (ppm)=0.85 (t, J=7 Hz, 3H, CH$_3$), 1.14–1.32 (m, 16H, (CH$_2$)$_8$), 1.56 (quint, J=7 Hz, 2H, C$\underline{H}_2$CH$_2$CO), 2.15 (s, 3H, PyrCH$_3$), 2.29 (s, 3H, PyrCH$_3$), 2.67 (t, J=7 Hz, 2H, CH$_2$C$\underline{H}_2$CO), 3.44 (s, 2H, PyrC$\underline{H}_2$COOH), 5.18 (s, 2H, NCH$_2$), 6.46 (d, J=16 Hz, 1H, CH=C$\underline{H}$CO), 6.92 (d, J=8 Hz, 2H, aromat. H), 7.54 (d, J=16 Hz, 1H, C$\underline{H}$=CHCO), 7.60 (d, J=8 Hz, 2H, aromat. H)

EXAMPLE 5

3-(4-{[2-(Carboxymethyl)-4-dodecanoyl-3,5-dimethyl-pyrrol-1-yl]methyl}phenyl)propionic acid Preparation as in Example 1C using 55 mg (0.1 mmol) of ethyl (E)-4-({3-dodecanoyl-5-[(ethoxy-carbonyl)methyl]-2,4-dimethylpyrrol-1-yl}methyl)-cinnamate (Example 4B) in place of ethyl (E)-4-dodecanoyl-1-{4-[2-(ethoxycarbonyl)ethenyl]pyrrole-2 -carboxylate. The product is precipitated from ether/petroleum ether.

Yield: 20 mg (48%). Melting point: 127–129° C. C$_{30}$H$_{43}$NO$_5$ (497.7).

$^1$H-NMR (CDCl$_3$): δ (ppm)=0.88 (t, J=7 Hz, 3H, CH$_3$), 1.18–1.43 (m, 16H, (CH$_2$)$_8$), 1.70 (quint, J=7 hz, 2H, C$\underline{H}_2$CH$_2$CO), 2.25 (s, 3H, PyrCH$_3$), 2.48 (s, 3H, PyrCH$_3$), 2.60 (t, J=8 Hz, 2H, CH$_2$) , 2.76 (T, J=7 Hz, 2H, CH$_2$) , 2.88 (t, J=8 Hz, 2H, CH$_2$, 3.50 (s, 2H, PyrC$\underline{H}_2$COOH), 5.07 (s, 2H, NCH$_2$), 6.82 (d, J=8 Hz, 2H, aromat. H), 7.09 (d, J=8 Hz, 2H, aromat. H)

EXAMPLE 6

(E)-4-{[2-(2-Carboxyethyl)-3,5-dimethyl-4-octadecanoyl-pyrrol-1-yl]methyl}cinnamic acid A. Ethyl (E)-4-[(2,4-dimethyl-3-octadecanoylpyrrol-1-yl) methyl]cinnamate Preparation as in Example 2C with 362 mg (1 mmol) of 2,4-dimethyl-3-octadecanoylpyrrole (Lehr M., WO95/13266) in place of 3-dodecanoyl-2,4-dimethylpyrrole and with ethyl (E)-4-(bromomethyl)-cinnamate in place of ethyl (E)-3-(bromo-methyl)cinnamate.

Yield: 300 mg (55%). Melting point: 53–55° C. C$_{36}$H$_{55}$NO$_3$ (549.8). MS (EI): m/z (rel.int.)=549 (7%), 325 (31%), 310 (28%), 189 (18%), 122 (100%).

$^1$H-NMR (CDCl$_3$): δ (ppm)=0.88 (t, J=7 hz, 3H, CH$_3$), 1.16–1.39 (m, 28H, (CH$_2$)$_{14}$), 1.34 (t, J=7 Hz, 3H, OCH$_2$C$\underline{H}_3$), 1.68 (quint, J=7 Hz, 2H, C$\underline{H}_2$CO$_2$CO), 2.28 (s, 3H, PyrCH$_3$), 2.40 (s, 3H, PyrCH$_3$), 2.72 (t, J=7 Hz, 2H, CH$_2$C$\underline{H}_2$CO), 4.26 (q, J=7 Hz, 2H, OC$\underline{H}_2$CH$_3$), 4.99 (s, 2H, NCH$_2$), 6.35 (s, 1H, aromat. H), 6.41 (d, J=16 Hz, 1H, CH=C$\underline{H}$CO), 7.01 (d, J=8 Hz, 2H, aromat. H), 7.47 (d, J=8 Hz, 2H, aromat. H), 7.64 (d, J=16 Hz, 1H, C$\underline{H}$=CHCO)

B. Ethyl (E)-4-({2-[2-(methoxycarbonyl)ethyl]-3,5-dimethyl-4-octadecanoylpyrrol-1-yl}methyl)cinnamate 0.1 ml of BF$_3$/ethyl ether complex is added to a solution of 275 mg (0.5 mmol) of (E)-4-[(2,4-dimethyl-3-octadecanoylpyrrol-1-yl)methyl]cinnamate and 0.25 ml of methyl acrylate in 5 ml of absol. nitrobenzene. The mixture is stirred at room temperature for 24 h. Addition of saturated NaCl solution is followed by extraction with ether. After drying over Na$_2$SO$_4$, the solvent is distilled off, and the residue is purified by CC (silica gel, 1. petroleum ether/ethyl acetate 9+1, 2. petroleum ether/ethyl acetate 8+2). The product fractions are concentrated; the remaining oil crystallizes after some time.

Yield: 250 mg (79%). Melting point: 72–74° C. C$_{40}$H$_{61}$NO$_5$ (635.9). MS (CI): m/z (rel.int.)=636 (4%), 448 (100%), 252 (84%).

$^1$H-NMR (CDCl$_3$): δ (ppm)=0.88 (t, J=7 Hz, 3h, CH$_3$), 1.13–1.39 (m, 28H, (CH$_2$)$_{14}$), 1.34 (t, J=7 Hz, 3H, OCH$_2$C$\underline{H}_3$), 1.69 (quint, J=7 Hz, 2H, C$\underline{H}_2$CH$_2$CO), 2.24 (s, 3h, PyrCH$_3$), 2.32 (t, J=7 Hz, 2H, CH$_2$), 2.37 (s, 3H, PyrCH$_3$), 2.73 (t, J=7 Hz, 2H, CH$_2$), 2.80 (t, J=7 Hz, 2H, CH$_2$), 3.63 (s, 3H, OCH$_3$), 4.26 (q, J=7 Hz, 2H, OC$\underline{H}_2$CH$_3$), 5.11 (s, 2H, NCH$_2$), 6.40 (d, J=16 Hz, 1H, CH=C$\underline{H}$CO), 6.87 (d, J=8 Hz, 2H, aromat. H), 7.46 (d, J=8 Hz, 2H, aromat. H), 7.64 (d, J=16 Hz, 1H, C$\underline{H}$=CHCO)

C. (E)-4-{[2-(2-Carboxyethyl)-3,5-dimethyl-4-octa-decanoyl-pyrrol-1-yl]methyl]}cinnamic acid Preparation as in Example 2E with 64 mg (0.1 mmol) of ethyl (E)-4-({2-[2-(methoxycarbonyl)-ethyl]-3,5-dimethyl-4-octadecanoylpyrrol-1-yl}methyl)-cinnamate in place of ethyl (E)-3-({3-dodecanoyl-5-[(ethoxycarbonyl)methyl]-2, 4-dimethylpyrrol-1-yl}-methyl)cinnamate. The product is precipitated from ether/petroleum ether.

Yield: 27 mg (45%). Melting point: 166–168° C. $C_{37}H_{55}NO_5$ (593.8).

$^1$H-NMR (CDCl$_3$): δ (ppm)=0.88 (t, J=7 Hz, 3H, CH$_3$), 1.17–1.42 (m, 28H, (CH$_2$)$_{14}$), 1.69 (quint, J=7 Hz, 2H, CH$_2$CH$_2$CO), 2.26 (s, 3H, PyrCH$_3$), 2.31 (s, 3H, PyrCH$_3$), 2.47 (t, J=7 Hz, 2H, CH$_2$), 2.74 (t, J=7 Hz, 2H, CH$_2$), 2.90 (t, J=7 Hz, 2H, CH$_2$), 5.16 (s, 2H, NCH$_2$), 6.25 (d, J=16 Hz, 1H, CH=CHCO), 6.85 (d, J=8 Hz, 2H, aromat. H), 7.44 (d, J=8 Hz, 2H, aromat. H), 7.57 (d, J=16 Hz, 1H, CH=CHCO)

EXAMPLE 7

3-(4-{[2-(2-Carboxyethyl)-3,5-dimethyl-4-octadecanoylpyrrol-1-yl]methyl}phenyl) propionic acid Preparation as in Example 1C using 64 mg (0.1 mmol) of ethyl (E)-4-({2-[2-(methoxycarbonyl)-ethyl]-3,5-dimethyl-4-octadecanoylpyrrol-1-yl}methyl)-cinnamate (Example 6B) in place of methyl (E)-4-dodecanoyl-1-{4-[2-(ethoxycarbonyl)-ethenyl]benzyl}-pyrrole-2-carboxylate. The product is precipitated from ether/petroleum ether.

Yield: 13 mg (22%). Melting point: 152–154° C. $C_{37}H_{57}NO_5$ (595.9).

$^1$H-NMR (CDCl$_3$): δ (ppm)=0.88 (t, J=7 Hz, 3H, CH$_3$), 1.18–1.42 (m, 28H, (CH$_2$)$_{14}$), 1.69 (quint, J=7 Hz, 2H, CH$_2$CH$_2$CO), 2.19–2.26 (m, 5H, CH$_2$ and PyrCH$_3$), 2.39 (s, 3H, PyrCH$_3$), 2.68 (t, J=7 Hz, 2H, CH$_2$), 2.73 (t, J=7 Hz, 2H, CH$_2$), 2.80 (t, J=7 Hz, 2H, CH$_2$), 2.92 (t, J=7 Hz, 2H, CH$_2$), 5.02 (s, 2H, NCH$_2$), 6.78 (d, J=8 Hz, 2H, aromat. H), 7.14 (d, J=8 Hz, 2H, aromat. H)

EXAMPLE 8

(E)-1-[3-(2-Carboxyethenyl)benzyl]-3-dodecanoylindole-2-carboxylic acid

A. Ethyl 3-dodecanoylindole-2-carboxylate

A mixture of 3.8 g (20 mmol) of ethyl indole-2-carboxylate, 6.0 g (30 mmol) of octadecanoic acid, 1.0 g of polyphosphoric acid, 20 ml of absol. CH$_2$Cl$_2$ and 4.4 ml of trifluoroacetic anhydride is stirred at room temperature for 4 h. Then 1 M NaOH is added, and the mixture is extracted with ether. The ether phase is dried over Na$_2$SO$_4$ and the solvent is distilled off. The product precipitates after addition of petroleum ether.

Yield; 4.3 g (58%). Melting point: 75–76° C. $C_{23}H_{33}NO_3$ (371.5). MS (EI): m/z (rel.int.)=371 (6%), 298 (60%), 216 (100%), 188 (42%), 170 (53%).

$^1$H-NMR (CDCl$_3$): δ (ppm)=0.88 (t, J=7 Hz, 3H, CH$_3$), 1.13–1.39 (m, 16H, (CH$_2$)$_8$), 1.43 (t, J=7 Hz, 3H, OCH$_2$CH$_3$), 1.74 (quint, J=7 Hz, 2H, CH$_2$CH$_2$CO), 3.06 (t, J=7 Hz, 2H, CH$_2$CH$_2$CO), 4.45 (q, J=7 Hz, 2H, OCH$_2$CH$_3$), 7.24 (t, J=8 Hz, 1H, aromat. H), 7.36 (d, J=8 Hz, 1H, aromat. H), 7.41 (t, J=8 Hz, 1H, aromat. H), 7.92 (d, J=8 Hz, 1H, aromat. H), 9.02 (s, 1H, NH)

B. Ethyl (E)-3-dodecanoyl-1-{3-[2-ethoxycarbonyl)-ethenyl]benzyl}indole-2-carboxylate Preparation as in Example 1B using 372 mg (1 mmol) of ethyl 3-dodecanoylindole-2-carboxylate in place of methyl 4-dodecanoylpyrrole-2-carboxylate and using ethyl (E)-3-(bromomethyl)cinnamate in place of ethyl (E)-4-(bromomethyl)cinnamate. The product is obtained as a waxy substance.

Yield: 393 mg (70%). $C_{35}H_{45}NO_5$ (559.7). MS (EI): m/z (rel.int.)=559 (11%), 486 (39%), 419 (100%), 189 (86%), 115 (38%).

$^1$H-NMR (CDCl$_3$) : δ (ppm)=0. 88 (t, J=7 Hz, 3H, CH$_3$), 1.18–1.48 (m, 22H, (CH$_2$)$_8$ and OCH$_2$CH$_3$ and OCH$_2$CH$_3$), 1.77 (quint, J=7 Hz, 2H, CH$_2$CH$_2$CO), 2.94 (t, J=7 Hz, 2H, CH$_2$CH$_2$CO), 4.25 (q, J=7 Hz, 2H, OCH$_2$CH$_3$), 4.36 (q, J=7 Hz, 2H, OCH$_2$CH$_3$), 5.57 (s, 2H, NCH$_2$), 6.37 (d, J=16 Hz, 1H, CH=CHCO), 7.09 (d, J=8 Hz, 1H, aromat. H), 7.21–7.34 (m, 5H, aromat. H), 7.43 (d, J=8 Hz, 1H, aromat. H), 7.59 (d, J=16 Hz, 1H, CH=CHCO), 7.96 (d, J=8 Hz, 1H, aromat. H)

C. (E)-1-[3-(2-Carboxyethenyl)benzyl]-3-dodecanoyl-indole-2-carboxylic acid

Preparation as in Example 2E with 56 mg (0.1 mmol) of ethyl (E)-3-dodecanoyl-1-{3-[2-(ethoxycarbonyl)ethenyl]benzyl}indole-2-carboxylate in place of ethyl (E)-3-({3-dodecanoyl-5-[(ethoxy-carbonyl)methyl]-2,4-dimethylpyrrol-1-yl}methyl)-cinnamate. The product is precipitated from ether. The product is precipitated from ether.

Yield: 21 mg (42%). Melting point: 186–187° C. $C_{31}H_{37}NO_5$ (503.6).

$^1$H-NMR ([D$_6$]-DMSO): δ (ppm)=0.85 (t, J=7 Hz, 3H, CH$_3$), 1.12–1.37 (m, 16H, (CH$_2$)$_8$), 1.63 (quint, J=7 Hz, 2H, CH$_2$CH$_2$CO), 2.91 (T, J=7 Hz, 2H, CH$_2$CH$_2$CO), 5.63 (s, 2H, NCH$_2$), 6.45 (d, J=16 Hz, 1H, CH=CHCO), 7.10 (d, J=8 Hz, 1H, aromat. H), 7.22–7.34 (m, 3H, aromat, H), 7.51 (d, J=16 Hz, 1H, CH=CHCO), 7.53–7.60 (m, 3H, aromat. H), 7.96 (d, J=8 Hz, 1H, aromat. H)

EXAMPLE 9

1-[3-(2-Carboxyethyl)benzyl]-3-dodecanoylindole-2-carboxylic acid

Preparation as in Example 1C using 56 mg (0.1 mmol) of ethyl (E)-3-dodecanoyl-1-{3-[2-(ethoxy-carbonyl)ethenyl]benzyl}indole-2-carboxylate (Example 8B) in place of methyl (E)-4-dodecanoyl-1-{4-[2-(ethoxycarbonyl)ethenyl]benzyl}pyrrole-2-carboxylate. The intermediate resulting from the hydrogenation is purified by CC (silica gel, petroleum ether/ethyl acetate 9+1). The product is precipitated from ether.

Yield: 11 mg (22%). Melting point: 131–132° C. $C_{31}H_{39}NO_5$ (505.7).

$^1$H-NMR ([D$_6$]-DMSO) δ (ppm)=0.85 (t, J=7 Hz, 3H, CH$_3$), 1.14–1.37 (m, 16H, (CH$_2$)$_8$), 1.63 (quint, J=7 Hz, 2H, CH$_2$CH$_2$CO), 2.48 (t, J=8 Hz, 2H, CH$_2$), 2.76 (t, J=8 Hz, 2H, CH$_2$), 2.90 (t, J=7 Hz, 2H, CH$_2$CH$_2$CO), 5.57 (s, 2H, NCH$_2$), 6;86 (d, J=8 Hz, 1H, aromat. H), 7.10 (d, J=8 Hz, 1H, aromat. H), 7.15–7.31 (m, 4H, aromat. H), 7.55 (d, J=8 Hz, 1H, aromat. H), 7.96 (d, J=8 Hz, 1H, aromat. H)

EXAMPLE 10

(E)-1-[4-(2-Carboxyethenyl)benzyl]-3-dodecanoylindole-2-carboxylic acid

A. Ethyl (E)-1-{4-[2-(ethoxycarbonyl)ethenyl]benzyl}-indole-2-carboxylate

A mixture of 378 mg (2 mmol) of ethyl indole-2-carboxylate, 269 mg (2.4 mmol) of potassium t-butoxide and 5 ml of absol. DMSO is stirred in an oil bath at 110° C. for 5 min. Then 538 mg (2 mmol) of ethyl (E)-4-(bromomethyl) cinnamate are added, and the mixture is heated at the same temperature for a further 10 min. Cooling and addition of water and NaCl are followed by extraction with CHCl$_3$ several times. The organic phases are dried over Na$_2$SO$_4$, the solvent is distilled off, and the product is isolated by CC (silica gel, petroleum ether/ethyl acetate 9+1). The product fractions are concentrated; the remaining oil crystallizes after some time.

Yield: 479 mg (63%). Melting point: 89–91° C. $C_{23}H_{23}NO_4$ (377.4). MS (EI): m/z (rel.int.)=377 (18%), 189 (100%), 115 (67%).

¹H-NMR (CDCl₃): δ (ppm)=1.32 (t, J=7 Hz, 3H, OCH₂CH₃), 1.36 (t, J=7 Hz, 3H, OCH₂CH₃), 4.24 (q, J=7 Hz, 2H, OCH₂CH₃), 4.32 (q, J=7 Hz, 2H, OCH₂CH₃), 5.85 (s, 2H, NCH₂), 6.35 (d, J=16 Hz, 1H, CH=CHCO), 7.05 (d, J=8 Hz, 2H, aromat. H), 7.16–7.20 (m, 1H, aromat. H), 7.29–7.34 (m, 2H, aromat. H), 7.40 (d, J=8 Hz, 2H, aromat. H), 7.41 (s, 1H, aromat. H), 7.61 (d, J=16 Hz, 1H, CH=CHCO), 7.72 (d, J=8 Hz, 1H aromat. H)

B. Ethyl (E)-3-dodecanoyl-1-{4-[2-(ethoxycarbonyl)-ethenyl]benzyl}indole-2-carboxylate A mixture of 377 mg (1 mmol) of ethyl 1-{4-[2-(ethoxycarbonyl)ethenyl]benzyl}indole-2-carboxylate, 300 mg (1.5 mmol) of dodecanoic acid, 67 mg of polyphosphoric acid, 5 ml of absol. CH₂Cl₂ and 0.33 ml of trifluoroacetic anhydride is stirred at room temperature for 4 h. Then 1 M NaOH is added, and the mixture is extracted with ether. The organic phase is dried over Na₂SO₄, the solvent is distilled off, and the product is isolated by CC (silica gel, petroleum ether/ethyl acetate 9+1). The product fractions are concentrated; the remaining oil crystallizes after some time.

Yield: 219 mg (39%). Melting point: 72–74° C. $C_{35}H_{45}NO_5$ (559.7). MS (EI): m/z (rel.int.)=559 (12%), 486 (35%), 419 (75%), 189 (100%), 115 (42%).

¹H-NMR (CDCl₃): δ (ppm)=0.88 (t, J=7 Hz, 3H, CH₃), 1.17–1.45 (m, 16H, (CH₂)₈), 1.28 (t, J=7 Hz, 3H, OCH₂CH₃), 1.32 (t, J=7 Hz, 3H, OCH₂CH₃), 1.76 (quint, J=7 Hz, 2H, CH₂CH₂CO), 2.93 (t, J=7 Hz, 2H, CH₂CH₂CO, 4.25 (q, J=7 Hz, 2H, OCH₂CH₃), 4.35 (q, J=7 Hz, 2H, OCH₂CH₃), 5.59 (s, 2H, NCH₂), 6.38 (d, J=16 Hz, 1H, CH=CHCO), 7.10 (d, J=8 Hz, 2H, aromat. H), 7.26–7.35 (m, 3H, aromat. H), 7.44 (d, J=8 Hz, 2H, aromat. H), 7.62 (d, J=16 Hz, 1H, CH=CHCO), 7.95 (d, J=8 Hz, 1H, aromat. H)

C. (E)-1-[4-(2-Carboxyethenyl)benzyl]-3-dodecanoyl-indole-2-carboxylic acid

Preparation as in Example 2E with 56 mg (0.1 mmol) of ethyl (E)-3-dodecanoyl-1-{4-[2-(ethoxy-carbonyl)ethenyl]benzyl}indole-2-carboxylate in place of ethyl (E)-3-({3-dodecanoyl-5-[(ethoxycarbonyl)-methyl]-2,4-dimethylpyrrol-1-yl}methyl)cinnamate. The product is precipitated from ether.

Yield: 15 mg (30%). Melting point: 224–230° C. $C_{31}H_{37}NO_5$ (503.6).

¹H-NMR ([D₆]-DMSO): δ (ppm)=0.85 (t, J=7 Hz, 3H, CH₃), 1.12–1.36 (m, 16H, (CH₂)₈), 1.63 (quint, J=7 Hz, 2H, CH₂CH₂CO), 2.91 (t, J=7 Hz, 2H, CH₂CH₂CO), 5.65 (s, 2H, NCH₂), 6.46 (d, J=16 Hz, 1H, CH=CHCO), 7.15 (d, J=8 Hz, 2H, aromat. H), 7.24 (t, J=8 Hz, 1H, aromat. H), 7.29 (t, J=8 Hz, 1H, aromat. H), 7.50–7.57 (m, 2H, CH=CHCO and aromat. H), 7.60 (d, J=8 Hz, 2H, aromat. H), 7.96 (d, J=8 Hz, 1H, aromat. H)

EXAMPLE 11

1-[4-(2-Carboxyethyl)benzyl]-3-dodecanoylindole-2-carboxylic acid

Preparation as in Example 1C using 56 mg (0.1 mmol) of ethyl (E)-3-dodecanoyl-1-{4-[2-(ethoxy-carbonyl)ethenyl]benzyl}indole-2-carboxylate (Example 10B) in place of methyl (E)-4-dodecanoyl-1-{4-[2-(ethoxycarbonyl)ethenyl]benzyl}pyrrole-2-carboxylate. The intermediate produced in the hydrogenation is purified by CC (silica gel, petroleum ether/ethyl acetate 1. 9+1, 2. 8+2). The product is precipitated from petroleum ether.

Yield: 17 mg (34%). Melting point: 168–169° C. $C_{31}H_{39}NO_5$ (505.7).

¹H-NMR (CDCl₃): δ (ppm)=0.88 (t, J=7 Hz, 3H, CH₃), 1.18–1.42 (m, 14H, (CH₂)₇), 1.48 (quint, J=7 Hz, 2H, CH₂CH₂CH₂CO), 1.88 (quint, J=7 Hz, 2H, CH₂CH₂CO), 2.62 (t, J=8 Hz, 2H, CH₂), 2.89 (t, J=8 Hz, 2H, CH₂), 3.31 (t, J=7 Hz, 2H, CH₂), 6.08 (s, 2H, NCH₂), 7.03 (d, J=8 Hz, 2H, aromat. H), 7.10 (d, J=8 Hz, 2H, aromat. H), 7.41–7.46 (m, 2H, aromat. H), 7.54–7.58 (m, 1H, aromat. H), 8.02–8.05 (m, 2H, aromat. H)

EXAMPLE 12

1-[4-(Carboxymethoxy)benzyl]-3-dodecanoylindole-2-carboxylic acid

A mixture of 223 mg (0.6 mmol) of ethyl 3-dodecanoylindole-2-carboxylate, 81 mg (0.72 mmol) of potasisum t-butoxide and 2 ml of absol. DMSO is stirred in an oil bath at 110° C. for 5 min. Then 197 mg (0.72 mmol) of ethyl 2-[4-(bromomethyl)phenoxy]acetate are added, and the mixture is heated at the same temperature for a further 10 min. Cooling and addition of water and NaCl are followed by extraction with ether. The organic phase is dried over Na₂SO₄, the solvent is distilled off, and the residue is chromato-graphed on silica gel with petroleum ether/ethyl acetate (9+1). The resulting ethyl 3-dodecanoyl-1-{4-[(ethoxycarbonyl)methoxy]benzyl}indole-2-carboxylate is hydrolyzed in analogy to Example 2E. The product is precipitated from ether.

Yield: 60 mg (20%). Melting point: 191–193° C. $C_{30}H_{37}NO_6$ (507.6).

¹H-NMR (CDCl₃): δ (ppm)=0.88 (t, J=7 Hz, 3H, CH₃), 1.18–1.42 (m, 14H, (CH₂)₇), 1.48 (quint, J=7 Hz, 2H, CH₂CH₂CH₂CO), 1.88 (quint, J=7 Hz, 2H, CH₂CH₂CO), 3.31 (t, J=7 Hz, 2H, CH₂CH₂CO), 4.61 (s, 2H, OCH₂CO), 6.06 (S, 2H, NCH₂), 6.82 (d, J=9 Hz, 2H, aromat. H), 7.10 (d, J=9 Hz, 2H, aromat. H), 7.43–7.47 (m, 2H, aromat. H), 7.56–7.59 (m, 1H, aromat. H), 8.02–8.05 (m, 2H, aromat. H)

EXAMPLE 13

1-{2-[3-(carboxymethyl)phenoxy]ethyl}-3-dodecanoyl-indole-2-carboxylic acid

Preparation as in Example 12 using 207 mg (0.72 mmol) of ethyl 2-[3-(2-bromoethoxy)phenyl]acetate in place of ethyl 2-[4-(bromomethyl)phenoxy]acetate. The product is precipitated from ether/petroleum ether.

Yield: 84 mg (27%). Melting point: 114–116° C. $C_{31}H_{39}NO_6$ (521.7).

¹H-NMR ([D₆]-DMSO): δ (ppm)=0.85 (t, J=7 Hz, 3H, CH₃), 1.13–1.34 (m, 16H, (CH₂)₈ ), 1.61 (quint, J=7 Hz, 2H, CH₂CH₂CO), 2.88 (t, J=7 Hz, 2H, CH₂CH₂CO), 3.47 (s, 2H, CH₂COOH), 4.23 (t, J=5 Hz, 2H, NCH₂CH₂O), 4.80 (t, J=5 Hz, 2H, NCH₂CH₂O), 6.71 (d, J=8 Hz, 1H, aromat. H), 6.72 (s, 1H, aromat. H), 6.79 (d, J=8 Hz, 1H, aromat. H), 7.16 (t, J=8 Hz, 1H, aromat. H), 7.25 (t, J=8 Hz, 1H, aromat. H), 7.36 (t, J=8 Hz, 1H, aromat. H), 7.74 (d, J=8 Hz, 1H, aromat. H), 7.93 (d, J=8 Hz, 1H, aromat. H)

EXAMPLE 14

1-{2-[4-(Carboxymethyl)phenoxy]ethyl}-3-dodecanoyl-indole-2-carboxylic acid

Preparation as in Example 12 using 207 mg (0.72 mmol) of ethyl 2-[4-(2-bromoethoxy)phenyl]acetate in place of ethyl 2-[4-(bromomethyl)phenoxy]acetate. The product is precipitated from petroleum ether.

Yield: 63 mg (20%). Melting point: 130–131° C. $C_{31}H_{39}NO_6$ (521.7).

$^1$H-NMR ([D$_6$]-DMSO): δ (ppm)=0.85 (t, J=7 Hz, 3H, CH$_3$), 1.13–1.37 (m, 16H, (CH$_2$)$_8$), 1.62 (quint, J=7 Hz, 2H, CH$_2$CH$_2$CO), 2.88 (t, J=7 Hz, 2H, CH$_2$CH$_2$CO), 3.43 (s, 2H, CH$_2$COOH), 4.23 (t, J=5 Hz, 2H, NCH$_2$CH$_2$O), 4.80 (t, J=5 Hz, 2H, NCH$_2$CH$_2$O), 6.76 (d, J=8 Hz, 2H, aromat. H), 7.10 (d, J=8 Hz, 2H, aromat. H), 7.24 (t, J=8 Hz, 1H, aromat. H), 7.36 (t, J=8 Hz, 1H, aromat. H), 7.72 (d, J=8 Hz, 1H, aromat. H), 7.92 (d, J=8 Hz, 1H, aromat. H)

EXAMPLE 15

The efficacy of the compounds according to the invention can be determined from the inhibition of phospholipase A$_2$. The assay method used has already been described (see Lehr M., In-vitro assay for the evaluation of phospholipase A$_2$ inhibitors using bovine platelets and HPLC with UV-detection. Pharm.Pharmacol. Lett. 1992, 2, 176–179). The test substances were normally dissolved in DMSO.

The results obtained on testing compounds according to the invention are listed in Table 5 below. The values for the inhibition by the already known PLA$_2$ inhibitors (S)-N-hexadecylpyrrolidine-2-carboxamide (McGregor et al., U.S. Pat. No. 4792555), 1-methyl-3-octadecanoylindole-2-carboxylic acid and 3-(1,3,5-trimethyl-4-octadecanoylpyrrole-2-yl)propionic acid (Lehr M., WO95/13266) with the test system used are indicated in Table 6.

TABLE 5

| Compound of Example No. | Inhibition of cytosolic PLA$_2$ IC$_{50}$ [μM] |
| --- | --- |
| 2 | 4.6 |
| 3 | 3.0 |
| 13 | 1.6 |
| 14 | 1.6 |

TABLE 6

| Compound | Inhibition of cytosolic PLA$_2$ IC$_{50}$ [μM] |
| --- | --- |
| (S)-N-Hexadecyl-2-pyrrolidinecarboxamide | 13 |
| 3-(1,3,5-Trimethyl-4-octadecanoylpyrrole-2-yl)propionic acid | 13 |
| 1-Methyl-3-octadecanoylindole-2-carboxylic acid | 8 |

What is claimed is:

1. A substituted pyrrole compound or a substituted indole compound of the formulae I and II:

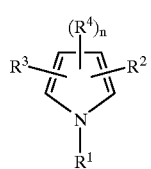

I

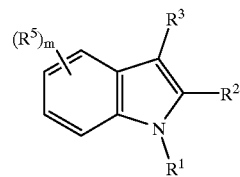

II in which

R$^1$ is a radical —Y$^1$—Ar—Y$^2$—Y$^3$ where Y$^1$ is a C$_1$–C$_{12}$-alkyl, C$_2$–C$_{12}$-alkenyl, C$_1$–C$_{12}$-alkoxy or C$_2$–C$_{12}$-alkenyloxy radical which is uninterrupted or interrupted by one or more oxygen atoms, Ar, is an aryl group which is unsubstituted or substituted by 1 to 3 substituents selected from the group of R$^6$, R$^7$ and R$^8$, Y$^2$ is a C$_1$–C$_{12}$-alkyl, C$_2$–C$_{12}$-alkenyl, C$_1$–C$_{12}$-alkoxy or C$_2$–C$_{12}$-alkenyloxy radical which is uninterrupted or interrupted by one or more oxygen atoms, and Y$^3$ is —COOR$^{17}$, —CONR$^{17}$R$^{17}$, —CONHCOR$^{19}$, —CONHS(O)$_2$R$^{19}$, —CONHNHS(O)$_2$R$^{19}$, or —Tz where Tz is 1H- or 2H-tetrazol-5-yl; R$^2$ is —COOR$^{17}$, —Y$^4$—COOR$^{17}$, —CONR$^{17}$R$^{17}$, —Y$^4$—Y$^4$—CONR$^{17}$R$^{17}$, —CONHCOR$^{19}$, —Y$^4$—CONHCOR$^{19}$, —CONHS(O)$_2$R$^{19}$, —Y$^4$—CONHS(O)$_2$R$^{19}$, —CONHNS(O)$_2$R$^{19}$, —Y$^4$—CONHNHS(O)$_2$R$^{19}$, —Tz or —Y$^4$—Tz where Y$^4$ is a C$_1$–C$_8$-alkyl or C$_2$–C$_8$-alkenyl group which is uninterrupted or interrupted by an oxygen atom, and Tz is 1H- or 2H-tetrazol-5-yl; R$^3$ is —CO—R$^9$ where R$^9$ is —Y$^5$, -aryl or —Y$^5$-aryl, where Y$^5$ is a C$_1$–C$_{19}$-alkyl, C$_2$–C$_{19}$-alkenyl or -alkynyl group which is uninterrupted or interrupted by one or more oxygen atoms and aryl is an aryl group which is unsubstituted or substituted by 1 to 3 substituents selected from the group of R$^{10}$, R$^{11}$ and R$^{12}$; each R$^4$ radical is, independently of the others, a hydrogen atom, a halogen atom, —CF$_3$, —Y$^6$, -aryl or —Y$^6$-aryl, where Y$^6$ is a C$_1$–C$_8$-alkyl or C$_2$–C$_8$-alkenyl or -alkynyl group which is uninterrupted or interrupted by one or more oxygen atoms, and aryl is an aryl group which is unsubstituted or substituted by 1 to 3 substituents selected from the group of R$^{13}$, R$^{14}$ and R$^{15}$, and n is the number 2; and where two Y$^6$ radicals can, if they are two adjacent alkyl radicals, form together with the carbon atom to which they are bonded a 5–8-membered ring which is unsubstituted or substituted by 1 to 2 C$_1$–C$_4$-alkyl groups; each R$^5$ radical is, independently of the others, a hydrogen atom or R$^{16}$, and m is the number 4;

R$^6$, R$^7$, R$^8$, R$^{10}$, R$^{11}$, R$^{12}$, R$^{13}$, R$^{14}$, R$^{15}$ and R$^{16}$ are selected independently of one another from:

(1) a C$_1$–C$_{20}$-alkyl group which is uninterrupted or interrupted by an oxygen atom;

(2) a C$_2$–C$_{20}$-alkenyl group which is uninterrupted or interrupted by an oxygen atom;

(3) a C$_2$–C$_{20}$-alkynyl group which is uninterrupted or interrupted by an oxygen atom;

(4) halogen;

(5) —CF$_3$;

(6) perhalo-C$_1$–C$_6$-alkenyl;

(7) —CN;

(8) —NO$_2$;

(9) —OR$^{17}$;

(10) —SR$^{17}$;

(11) —COOR$^{17}$;

(12) —COR$^{18}$;

(13) —COCH$_2$OH;

(14) —NHCOR$^{17}$;
(15) —NR$^{17}$R$^{17}$;
(16) —NHS(O)$_2$R$^{17}$;
(17) —SOR$^{17}$;
(18) —S(O)$_2$R$^{17}$;
(19) —CONR$^{17}$R$^{17}$;
(20) —SO$_2$NR$^{17}$R$^{17}$;
(21) —OOCR$^{18}$;
(22) —OOCNR$^{17}$R$^{17}$;
(23) —OOCOR$^{17}$;
(24) —(CH$_2$)$_r$OR$^{23}$;
(25) —(CH$_2$)$_r$SR$^{23}$;
(26) —(CH$_2$)$_r$NHR$^{23}$;
(27) —(CH$_2$)$_s$R$^{20}$;

R$^{17}$ is in each case, independently of one another, hydrogen, a C$_1$–C$_{20}$-alkyl or C$_2$–C$_{19}$-alkenyl or -alkynyl group which is uninterrupted or interrupted by an oxygen atom or —(CH$_2$)$_t$R$^{20}$;

R$^{18}$ is in each case, independently of one another, R$^{17}$, —CF$_3$, —(CH$_2$)$_u$COOH or —(CH$_2$)$_u$COO R$^{21}$;

R$^{19}$ is in each case, in dependently of one another, R$^{17}$ or —CF$_3$;

R$^{20}$ is in each case, independently of one another, aryl substituted by one or two R$^{22}$ groups;

R$^{21}$ is in each case, independently of one another, C$_1$–C$_6$-alkyl, benzyl or phenyl;

R$^{22}$ is in each case, independently of one another, hydrogen, halogen, C$_1$–C$_{12}$-alkyl, C$_1$–C$_{12}$-alkoxy, C$_1$–C$_{12}$-alkylthio, C$_1$–C$_{12}$-alkylsulfonyl, C$_1$–C$_{12}$-alkylcarbonyl, —CF$_3$, —CN or —NO$_2$;

R$^{23}$ is in each case, independently of one another, hydrogen or —COR$^{21}$;

r is 1 to 20;

s and t are, in each case, independently of one another, 0 to 12;

u is 0 to 4;

or the pharmaceutically suitable salts or esters thereof.

2. A compound as claimed in claim 1, in which Y$^1$ is a methylene or ethylene group, Ar is a phenylene group, and Y$^2$ is an ethenylene or ethylene group in the position meta or para to Y$^1$.

3. A compound selected from the group consisting of 1-[4-(2-carboxyethyl)benzyl]-4-dodecanoylpyrrole-2-carboxylic acid, (E)-3-{[2-(carboxy-methyl)-4-dodecanoyl-3,5-dimethylpyrrol-1-yl]methyl}cinnamic acid, 3-(3-{[2-(carboxy-methyl)-4-dodecanoyl-3,5-dimethylpyrrol-1-yl] methyl}phenyl) propionic acid, (E)-4-{[2-(carboxymethyl)-4-dodecanoyl-3,5-dimethylpyrrol-1-yl]methyl}cinnamic acid, 3-(4-{[2-(carboxymethyl)-4-dodecanoyl-3,5-dimethylpyrrol-1-yl]methyl}phenyl)propionic acid, (E)-4-{[2-(2-carboxyethyl)-3,5-dimethyl-4-octadecanoylpyrrol-1-yl]methyl}cinnamic acid and 3-(4-{[2-(2-carboxyethyl)-3,5-dimethyl-4-octadecanoylpyrrol-1-yl]methyl}phenyl) propionic acid.

4. A compound as claimed in claim 1 of the formula II':

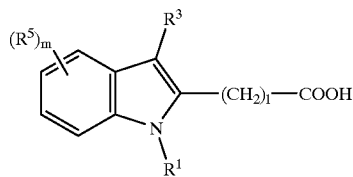

II' in which 1 is an integer from 0 to 3.

5. A compound as claimed in claim 4, in which R$^3$ is a (C$_{7-17}$-alkyl)—CO— or (aryl-C$_{1-17}$-alkyl)—CO— group.

6. A compound as claimed in claim 5, in which R$^3$ is a dodecanoyl group.

7. A compound as claimed in claim 4, in which 1 is the number 0.

8. A compound as claimed in claim 4, in which three R$^5$ radicals are a hydrogen atom, and the other R$^5$ radical is a hydrogen atom, a 4-chloro, 5-chloro or 5-methoxy group.

9. A compound as claimed in claim 4, in which the Y$^1$ radical of the R$^1$ radical is a methylene or ethoxy group, Ar is a phenylene group, and Y$^2$ is a methylene, ethylene, ethenylene or a methoxy group.

10. A compound as claimed in claim 4, selected from the group consisting of (E)-1-[3-(2-carboxyethen-1-yl)benzyl]-3-dodecanoyl-indole-2-carboxylic acid, 1-[3-(2-carboxyethyl)benzyl]-3-dodecanoylindole-2-carboxylic acid, (E)-1-[4-(2-carboxyethen-1-yl) benzyl]-3-dodecanoylindole-2-carboxylic acid, 1-[4-(2-carboxyethyl)benzyl]-3-dodecanoyl-indole-2-carboxylic acid, 1-[4-(2-carboxymethoxy)benzyl]-3-dodecanoylindole-2-carboxylic acid, 1-{2-[3-(carboxymethyl)phenoxy]ethyl}-3-dodecanoyl-indole-2-carboxylic acid and 1-{2-[4-(carboxymethyl)-phenoxy]ethyl}-3-dodecanoylindole-2-carboxylic acid.

11. A pharmaceutical comprising at least one compound as claimed in claim 1 containing pharmaceutically suitable excipients, pharmaceutically suitable additives or mixtures of such excipients and additives.

12. A process for preparing a substituted pyrrole compound and substituted indole compound as claimed in claim 1, in which a pyrrole compound or an indole compound of the formula 3' or 4'

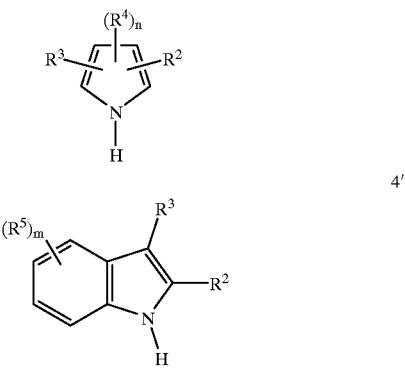

is alkylated with the alkyl halide Hal—Y$^1$-aryl —Y$^2$—Y$^3$, in the presence of a base, where the radicals R$^2$, R$^3$, R$^4$, R$^5$, Y$^1$, Y$^2$, Y$^3$ and aryl, and m and n are as defined in claim 1, and Hal is a halogen atom.

13. A process as claimed in claim 12 wherein the halogen atom is a bromine atom.

14. A process for inhibiting the activity of phospholipase A$_2$ in a subject which comprises administering to the subject a pharmaceutically effective amount of a pharmaceutical as claimed in claim 11.

15. A process for producing a pharmaceutical in a form suitable for administration to a subject which comprises preparing at least one compound as claimed in claim 1 and mixing such compound with suitable pharmaceutical excipients, suitable pharmaceutical additives or mixtures of such excipients and additives.

* * * * *